(12) United States Patent
Phillips et al.

(10) Patent No.: US 8,865,692 B2
(45) Date of Patent: Oct. 21, 2014

(54) COMPOSITIONS FOR THE TREATMENT OF GASTROINTESTINAL INFLAMMATION

(75) Inventors: Elaine Phillips, San Diego, CA (US); Malcolm Hill, Solana Beach, CA (US)

(73) Assignee: Meritage Pharma, Inc, San Diego, CA (US)

( * ) Notice: Subject to any disclaimer, the term of this patent is extended or adjusted under 35 U.S.C. 154(b) by 962 days.

(21) Appl. No.: 12/269,650

(22) Filed: Nov. 12, 2008

(65) Prior Publication Data

US 2009/0137540 A1   May 28, 2009

Related U.S. Application Data

(60) Provisional application No. 61/035,348, filed on Mar. 10, 2008, provisional application No. 61/054,103, filed on May 16, 2008, provisional application No. 61/054,105, filed on May 16, 2008, provisional application No. 61/012,012, filed on Dec. 6, 2007, provisional application No. 61/054,107, filed on May 16, 2008, provisional application No. 61/015,998, filed on Dec. 21, 2007, provisional application No. 61/019,818, filed on Jan. 8, 2008, provisional application No. 61/034,941, filed on Mar. 7, 2008, provisional application No. 61/054,106, filed on May 16, 2008, provisional application No. 61/090,568, filed on Aug. 20, 2008, provisional application No. 60/987,720, filed on Nov. 13, 2007, provisional application No. 61/054,104, filed on May 16, 2008.

(51) Int. Cl.
*A61K 31/56*  (2006.01)
*A61K 9/00*   (2006.01)
*A61K 31/58*  (2006.01)

(52) U.S. Cl.
CPC .................. *A61K 31/58* (2013.01); *A61K 9/006* (2013.01); *A61K 9/0065* (2013.01)
USPC .......................................... 514/182; 514/171

(58) Field of Classification Search
USPC .................................................. 514/171, 182
See application file for complete search history.

(56) References Cited

U.S. PATENT DOCUMENTS

| | | | |
|---|---|---|---|
| 2,861,920 | A | 11/1958 | Dale et al. |
| 4,684,534 | A | 8/1987 | Valentine |
| 4,880,796 | A | 11/1989 | Yamahira et al. |

(Continued)

FOREIGN PATENT DOCUMENTS

| | | |
|---|---|---|
| EP | 1201242 A2 | 5/2002 |
| EP | 1201242 A3 | 5/2002 |

(Continued)

OTHER PUBLICATIONS

Liacouras, Journal of Pediatric Gastroenterology and Nutrition, 1998;26(4):380-385.*

(Continued)

*Primary Examiner* — San-Ming Hui
(74) *Attorney, Agent, or Firm* — Wilson Sonsini Goodrich & Rosati

(57) ABSTRACT

Provided herein are methods for treating, preventing or alleviating the symptoms of and inflammation associated with inflammatory diseases and conditions of the gastrointestinal tract, for example, those involving the esophagus. Also provided herein are pharmaceutical compositions useful for the methods of the present invention.

1 Claim, 1 Drawing Sheet

(56) References Cited

U.S. PATENT DOCUMENTS

| | | |
|---|---|---|
| 4,900,552 A | 2/1990 | Sanvordeker et al. |
| 4,985,418 A | 1/1991 | Richards |
| 5,254,594 A | 10/1993 | Niikura et al. |
| 5,288,497 A | 2/1994 | Stanley et al. |
| 5,380,535 A | 1/1995 | Geyer et al. |
| 5,446,070 A | 8/1995 | Mantelle |
| 5,585,108 A | 12/1996 | Ruddy |
| 5,607,662 A | 3/1997 | Baskeyfield et al. |
| 5,643,602 A | 7/1997 | Ulmius |
| 5,679,390 A | 10/1997 | Conover |
| 5,711,936 A | 1/1998 | Hill et al. |
| 5,763,910 A | 6/1998 | Ema |
| 5,814,330 A | 9/1998 | Putteman et al. |
| 5,837,713 A | 11/1998 | Gleich |
| 5,840,332 A | 11/1998 | Lerner et al. |
| 5,855,913 A | 1/1999 | Hanes et al. |
| 5,863,910 A | 1/1999 | Bolonick et al. |
| 5,889,028 A | 3/1999 | Sandborn et al. |
| 5,985,309 A | 11/1999 | Edwards et al. |
| 6,028,095 A | 2/2000 | Guglietta |
| 6,248,363 B1 | 6/2001 | Patel et al. |
| 6,291,445 B1 | 9/2001 | Nilsson et al. |
| 6,306,789 B1 | 10/2001 | Dettmar et al. |
| 6,348,502 B1 | 2/2002 | Gardiner et al. |
| 6,387,383 B1 | 5/2002 | Dow et al. |
| 6,495,167 B2 | 12/2002 | Yang |
| 6,509,028 B2 | 1/2003 | Williams et al. |
| 6,562,363 B1 | 5/2003 | Mantelle et al. |
| 6,565,054 B2 | 5/2003 | Weesner et al. |
| 6,589,551 B1 | 7/2003 | Jolliffe |
| 6,589,556 B2 | 7/2003 | Cherukuri |
| 6,596,261 B1 | 7/2003 | Adjei et al. |
| 6,598,603 B1 | 7/2003 | Andersson et al. |
| 6,638,521 B2 | 10/2003 | Dobrozsi |
| 6,787,529 B2 | 9/2004 | Hoy et al. |
| 6,899,099 B2 | 5/2005 | Andersson et al. |
| 6,916,485 B2 | 7/2005 | Aiache et al. |
| 6,923,988 B2 | 8/2005 | Patel et al. |
| 6,962,717 B1 | 11/2005 | Huber et al. |
| 6,986,904 B2 | 1/2006 | Nilsson et al. |
| 7,063,862 B2 | 6/2006 | Lin et al. |
| 7,229,641 B2 | 6/2007 | Cherukuri |
| 7,288,267 B2 | 10/2007 | Bosch et al. |
| 7,361,646 B2 | 4/2008 | Belanoff |
| 7,544,348 B2 | 6/2009 | Jacob et al. |
| 7,547,433 B2 | 6/2009 | Jacob et al. |
| 7,799,331 B2 | 9/2010 | Asotra |
| 8,206,727 B2 | 6/2012 | Asotra |
| 8,324,192 B2 | 12/2012 | Dohil et al. |
| 8,497,258 B2 | 7/2013 | Dohil et al. |
| 8,679,545 B2 | 3/2014 | Dohil et al. |
| 2001/0016577 A1 | 8/2001 | Dobrozsi et al. |
| 2001/0029255 A1 | 10/2001 | Lindberg et al. |
| 2001/0049366 A1 | 12/2001 | Singh |
| 2002/0128216 A1 | 9/2002 | Dean et al. |
| 2002/0132803 A1 | 9/2002 | Dedhya et al. |
| 2002/0168334 A1 | 11/2002 | Jacob et al. |
| 2003/0013693 A1 | 1/2003 | Guivarc'h et al. |
| 2003/0017189 A1 | 1/2003 | Wong et al. |
| 2003/0055028 A1 | 3/2003 | Stergioupoulos et al. |
| 2003/0073676 A1 | 4/2003 | Biggadike et al. |
| 2003/0192533 A1 | 10/2003 | Andersson et al. |
| 2003/0215496 A1 | 11/2003 | Patel et al. |
| 2004/0023935 A1 | 2/2004 | Banerjee et al. |
| 2004/0053894 A1 | 3/2004 | Mazess et al. |
| 2004/0115133 A1 | 6/2004 | Wermeling |
| 2004/0141949 A1 | 7/2004 | Rosenthal et al. |
| 2004/0228919 A1 | 11/2004 | Houghton et al. |
| 2005/0042282 A1 | 2/2005 | Ieni |
| 2005/0049459 A1 | 3/2005 | Hern |
| 2005/0079138 A1 | 4/2005 | Chickering et al. |
| 2005/0095271 A1 | 5/2005 | Mathewson |
| 2005/0152847 A1 | 7/2005 | Trofast et al. |
| 2005/0153020 A1 | 7/2005 | Hamre et al. |
| 2005/0153946 A1 | 7/2005 | Hirsh et al. |
| 2005/0158383 A1 | 7/2005 | Boehm et al. |
| 2005/0208110 A1 | 9/2005 | Singh et al. |
| 2005/0239845 A1 | 10/2005 | Proehl et al. |
| 2005/0281772 A1 | 12/2005 | Bromley et al. |
| 2005/0287181 A1 | 12/2005 | Murthy |
| 2006/0013873 A1 | 1/2006 | Yang et al. |
| 2006/0024238 A1 | 2/2006 | Barth |
| 2006/0128655 A1 | 6/2006 | Falk et al. |
| 2006/0193783 A1 | 8/2006 | Bhowmick et al. |
| 2006/0216353 A1 | 9/2006 | Liversidge et al. |
| 2006/0235053 A1 | 10/2006 | Gebauer |
| 2007/0020196 A1 | 1/2007 | Pipkin et al. |
| 2007/0031459 A1 | 2/2007 | Asotra et al. |
| 2007/0104785 A1 | 5/2007 | Navale et al. |
| 2007/0111978 A1 | 5/2007 | Dohil et al. |
| 2007/0134280 A1 | 6/2007 | Roman et al. |
| 2007/0248548 A1 | 10/2007 | Blondino et al. |
| 2007/0259037 A1 | 11/2007 | Guivarc'h et al. |
| 2008/0008762 A1 | 1/2008 | Robinson et al. |
| 2008/0132580 A1 | 6/2008 | Mandavilli et al. |
| 2008/0207771 A1 | 8/2008 | Dikstein |
| 2008/0226736 A1 | 9/2008 | Caponetti et al. |
| 2009/0123390 A1 | 5/2009 | Hill et al. |
| 2009/0123550 A1 | 5/2009 | Phillips et al. |
| 2009/0123551 A1 | 5/2009 | Phillips et al. |
| 2009/0131386 A1 | 5/2009 | Phillips et al. |
| 2009/0137540 A1 | 5/2009 | Phillips et al. |
| 2009/0143343 A1 | 6/2009 | Hill et al. |
| 2009/0148554 A1 | 6/2009 | Kataoka et al. |
| 2009/0149433 A1 | 6/2009 | Phillips et al. |
| 2009/0181099 A1 | 7/2009 | Dohil et al. |
| 2009/0191275 A1 | 7/2009 | Dohil et al. |
| 2009/0264392 A1 | 10/2009 | Warndahl |
| 2010/0216754 A1 | 8/2010 | Hill et al. |
| 2011/0081411 A1 | 4/2011 | Perrett et al. |
| 2011/0097401 A1 | 4/2011 | Phillips et al. |
| 2012/0164080 A1 | 6/2012 | Hill et al. |
| 2013/0096096 A1 | 4/2013 | Dohil et al. |
| 2013/0296286 A1 | 11/2013 | Dohil et al. |

FOREIGN PATENT DOCUMENTS

| | | |
|---|---|---|
| EP | 1428526 | 6/2004 |
| EP | 1795183 A1 | 8/2006 |
| JP | 6-107550 | 4/1994 |
| JP | 2001-523638 | 11/2001 |
| JP | 2001-526210 | 12/2001 |
| JP | 2002-519318 | 7/2002 |
| JP | 2005-507000 | 3/2005 |
| JP | 2005-508976 | 4/2005 |
| WO | WO-99-18938 | 4/1999 |
| WO | WO-99-32156 A2 | 7/1999 |
| WO | WO-99-32156 A3 | 7/1999 |
| WO | WO-99-39699 | 8/1999 |
| WO | WO-99-40906 | 8/1999 |
| WO | WO-00-10528 | 3/2000 |
| WO | WO-01-37808 | 5/2001 |
| WO | WO-01-41748 | 6/2001 |
| WO | WO-02-09637 A2 | 2/2002 |
| WO | WO-02-24205 | 3/2002 |
| WO | WO-02-34235 | 5/2002 |
| WO | WO-02-064113 | 8/2002 |
| WO | WO-02-074316 | 9/2002 |
| WO | WO-03-057194 | 7/2003 |
| WO | WO-2004-030652 | 4/2004 |
| WO | WO-2004-045612 A1 | 6/2004 |
| WO | WO-2004-069225 | 8/2004 |
| WO | WO-2004-082590 | 9/2004 |
| WO | WO-2004-082590 A2 | 9/2004 |
| WO | WO-2005-056066 | 6/2005 |
| WO | WO-2005-065185 | 7/2005 |
| WO | WO-2005-074930 A1 | 8/2005 |
| WO | WO-2005-120517 | 12/2005 |
| WO | WO-2006-009825 | 1/2006 |
| WO | WO-2006-035418 | 4/2006 |
| WO | WO-2006-048736 | 5/2006 |
| WO | WO-2006-051980 | 5/2006 |
| WO | WO-2006-055954 A2 | 5/2006 |
| WO | WO-2006-085101 A2 | 8/2006 |

(56) References Cited

FOREIGN PATENT DOCUMENTS

| | | |
|---|---|---|
| WO | WO-2006-099591 A1 | 9/2006 |
| WO | WO-2006-103702 | 10/2006 |
| WO | WO-2007-061803 | 5/2007 |
| WO | WO-2007-075475 | 7/2007 |
| WO | WO-2007-096906 | 8/2007 |
| WO | WO-2008-005802 | 1/2008 |
| WO | WO-2008-070129 A2 | 6/2008 |
| WO | WO-2008-091855 | 7/2008 |
| WO | WO-2009-064417 | 5/2009 |
| WO | WO-2009-064819 A2 | 5/2009 |
| WO | WO-2009-132048 | 10/2009 |
| WO | WO-2011-041509 | 4/2011 |

OTHER PUBLICATIONS

Furuta, Journal of Pediatric Gastroenterology & Nutrition, 1998;26(4):468-471.*
Dobrozsi et al., International Journal of Pharmaceutics, 1999;189:81-89.*
Ashorn et al., "The Natural Course of Gastroesophageal Reflux Disease in Children," Scand. J. Gastroenterol. 37(6):638-641 (2002).
Campieri et al., "Oral budesonide is as effective as oral prednisolone in active Crohn's disease," Gut 41:209-214 (1997).
Cortina et al., "Caustic esophagitis in children," An Esp Pediatr. 36(3):205-207 (1992).
Hanauer, S.B., "Therapy Update: New steroids for IBD: progress report," Gut 51:182-183 (2002).
Hellers, et al., "Oral Budesonide for Prevention of Postsurgical Recurrence in Crohn's Disease," Gastroenterol. 116:294-300 (1999).
Khan et al., "Esoinophilic Gastroenteritis. Epidemiology, Diagnosis and Management," Pediatr. Drugs 4(9):563-570 (2002).
Konikoff et al., "A Randomized, Double-Blind, Placebo-Controlled Trial of Fluticasone Propionate for Pediatric Eosinophilic Esophagitis," Gastroenterol. 131:1381-1391 (2006).
Li et al., "Clinical and endoscopic features of Chinese reflux esophagitis patients," World J. Gastroenterol,. 14(12):1866-1871 (2008).
Sharpe, S.A. et al., "Comparison of the Flow Properties of Aqueous Suspension Corticosteroid Nasal Sprays Under Differing Sampling Conditions," Drug Dev. Industrial Pharmacy 29(9):1005-1012 (2003).
Sicherer, S.H., "Clinical Aspects of Gastrointestinal Food Allergy in Childhood," Pediatr. 111(6):1609-1616 (2003).
GB0911779.7 Search Report dated Aug. 18, 2009.
Rowe et al., Handbook of Pharmaceutical Excipients, Jan. 1, 2006, Pharmaceutical Press, pp. 442-445.
PCT/US08/83290 Search Report dated Jul. 15, 2009.
PCT/US09/41316 Search Report dated Oct. 30, 2009.
Wang (Blanchard) et al., "Eotaxin-3 and a uniquely conserved gene-expression profile in eosinophilic esophagitis," J. Clin Invest. 116(2):536-547 (2006).
Watts, et al., "Targittm technology coated starch capsules for site-specific drug delivery into the lower gastrointestinal tract," Exp. Op. Drug Delivery 2(1):159-167 (2005) (Abstract).
Caro, J.J. et al., "Healing and relapse rates in gastroesophageal reflux disease treated with the newer proton-pump inhibitors lansoprazole, rabeprazole, and pantoprazole compared with omeprazole, ranitidine, and placebo: evidence from randomized clinical trials," Clin. Thera. 23(7):998-1017 (2001).
PCT/US08/83288 Search Report dated May 18, 2009.
PCT/US08/12783 Search Report dated Jun. 16, 2009.
PCT/US08/12781 Search Report dated Jun. 25, 2009.
PCT/US08/12780 Search Report dated Jun. 25, 2009.
PCT/US08/12712 Search Report dated Jun. 25, 2009.
Zhang, L. and Batchelor, H.K., "A bioadhesive formulation for the delivery of antifungal agents to the oesophagus," JPP 56(Suppl.): Poster Session 1 (2004).
U.S. Appl. No. 12/426,858, filed, Apr. 20, 2009.

Neumann et al., "A new therapy for eosinophilic esophagitis in adults: Efficacy of budesonide—Rincinol gel for 6 weeks in patients with dysphagia," Am J Gastroenterology 103(Suppl %):S8-S9 (2008).
Pasha et al., "Current concepts and treatment options in eosinophilic esophagitis," Curr Op Invest Drugs 7(11):992-996 (2006).
EP09734222 Supplementary Search Report and Written Opinion mailed Jul. 4, 2011.
Ciaccio et al., "Effect of the dose of oral hydrocortisone on growth rate during long-term treatment of children with salt losing congenital adrenal hyperplasia," Medicina, Buenos Aires 2002:62:551-554.
Copley et at "Understanding the relationship between formulation viscosity and nebulizer performance," poster presented at DDL 19, Dec. 10-12, 2008 (Edinburg, Scotland) [online][retrieved on Aug. 27, 2012]. Retrieved from the Internet:<URL:http://www.malvern.com/common/downloads/campaign/FormulationViscosity_NebuliserPerformance.pdf>.
DeMuth, "Treatment of Allergic Esophagitis with Budesonide Turbuhaler," J. Allergy Clin. Immunol., 113(2Suppl);S316 (2004)(Abstract Only).
Fawcett et al., "Stability of Hydrocortisone Oral Suspensions Prepared from Tablets and Powder," Annals of Pharmacotherapy, 29(10):987-990 (1995).
Garcia et al., "Viscosity measurements of nectar- and honey-thick liquids: product, liquid, and time comparisons," Dysphagia, 20:325-335 (2005).
Jiang et al., "Effects of antireflux treatment on bronchial hyper-responsiveness and lung function in asthmatic patients with gastroesophageal reflux disease," World Journal of Gastroenterology 9:1123-1125 (2003).
Lotong et al., "Texture and flavor characteristics of beverage containing commercial thickening agents for dysphagia diets," Journal of Food Science, 68(4):1537-1541 (2003).
Martin, Physical Pharmacy, $4^{th}$ Ed., p. 423, (1993) published by Lea & Febiger.
McCallion et al. (Exhibit C), "Nebulization of fluids of different physicochemical properties with air-jet and ultrasonic nebulizers," Pharm. Res. 12:1682-1688 (1995).
Noel et al., "Clinical and Immunopathologic Effects of Swallowed Flutlcasone for Eosinophilic Esophagitis," Clinical Gastroenterology and Hepatology, 2004, vol. 2, pp. 568-575.
Noureddini et al., "Viscosities of Vegetable Oils and Fatty Acids," JAOCS, 69(12):1189-1191 (1992).
Pulmicort Turbuhaler monograph, AstraZeneca, Dec. 2001.
Pulmicort Respules® (booklet Approval 2000, pp. 1-23).
AstraZeneca, Pulmicort Respules, Mar. 2004, AstraZeneca, pp. 1-4.
Szefler, Pharmacodynamics and Pharmacokinetics of budesonide: A new nebulized corticosteroid, Oct. 1999, Journal Allergy and Clinical Immunology, vol. 104, pp. S175-S182.
Dickman et al. The American Journal of Gastroenterology (2006) 101: 2463-2469.
CA App. No. 2,704,946 Examiner's Report dated Nov. 22, 2011.
CA App. No. 2,704,946 Examiner's Report dated Jun. 18, 2012.
International Preliminary Report for PCT App. PCT/US2008/83288 dated May 18, 2010.
AU App. No. 2008321030 Examiner's Report dated Apr. 8, 2011.
PCT/US11/41871 Search Report dated Feb. 9, 2012.
PCT/US10/038411 Search Report dated Mar. 22, 2011.
Aceves et al., "Prospective Analysis of an Abdominal Symptom Scoring Tool's Efficacy in the Clinical Distinction of Pediatric Eosinophilic Esophagitis from Gastroesophageal Reflux Disease," J. Allergy Clin. Immunol. Feb. 2008, S70 Abstracts No. 270.
Aceves, SS et al., "Oral viscous budesonide: A potential new therapy for eosinophilic esophagitis," Amer. Journal of Gastroenterology 2007; 102:1-9.
Aceves, S et al., "Distinguishing Eosinophilic Esophagitis in pediatric patients: clinical, endoscopic, and histologic features of an emerging disorder," Journal of Clinical Gastroenterology 2006; 41(3):252-6.
Aceves, SS et al. "Topical viscous budesonide suspension for treatment of eosinophilic esophagitis," J. Allergy Clin. Immunol. 2005; 116:705-6.

(56) References Cited

OTHER PUBLICATIONS

Batchelor, H.K. et al., "An in vitro mucosal model for prediction of the bioadhesion of alginate solutions to the oesophagus," Intl. J. Pharma. 238:123-132 (2002).
Batchelor, H.K. et al., "Feasibility of a bioadhesive drug delivery system targeted to oesophageal tissue," Eur. J. Pharmaceutics Biopharma. 57:295-298 (2004).
Batchelor, H., "Bioadhesive Dosage Forms for Esophageal Drug Delivery," Pharma. Res. 22(2):175-181 (2005).
Bogaart, H.C.A. et al., "Viscosity Is Not a Parameter of Postdeglutitve Pharyngeal Residue: Quantification and Analysis with Scintigraphy,", Dysphagia 22:145-149 (2007).
Bonis, P.A. et al., "Eosinophilic esophagitis," http://www.uptodate.com/online/content/topic.do?topicKey=eso_dis./11927 &view=print, 2008.
Budin, C et al. "Eosinophilic esophagitis: 3 case reports," Gastroenterol. Clin. Biol. 2005; 29:73-5.
Cheung, K M et al., "Esophageal eosinophilia in children with dysphagia," J. Pediatr. Gastroenterol. Nutr. 2003;37:498-503.
Cherian S et al., "Rapidly increasing prevalence of eosinophilic oesophagitis in Western Australia," Arch. Dis. Child 2006; 91:1000-4.
Christup, L.L. et al., "Deposition of a model substance, $^{99m}$Tc E-HIDA, in the oral cavity after administration of lozenges, chewing gum and sublingual tablets," Intl. J. Pharmaceutics 66:169-174 (1990).
Collaud, S. et al., "Clinical evaluation of bioadhesive hydrogels for topical delivery of hexylaminolevulinate to Barrett's esophagus," J. Controlled Release 123:203-210 (2007).
Croese J et al., "Clinical and endoscopic features of eosinophilic esophagitis in adults," Gastrointest. Endosc. 2003; 58:516-22.
Desai T K et al., "Association of eosinophilic inflammation with esophageal food impaction in adults," Gastrointest. Endosc. 2005; 61:795-801.
Dobroszi, D. et al., "Comparative mucoretention of sucralfate suspensions in an everted rat esophagus model," Intl. J. Pharmaceutics 189:81-89 (1999).
Dohil R et al., "The evaluation and treatment of gastrointestinal disease in children with cystinos is receiving cysteamine," J. Pediatr. 2003; 14:224-30.
Faubion W A, Jr. et al., "Treatment of eosinophilic esophagitis with inhaled corticosteroids," J. Pediatr. Gastroenterol. Nutr. 1998; 27:90-3.
Fogg M I et al., "Pollen and eosinophilic esophagitis," J. Allergy Clin. Immunol. 2003; 112:796-7.
Fox V L et al., "Eosinophilic esophagitis: it's not just kid's stuff," Gastrointest. Endosc. 2002; 56:260-70.
Furuta, GT et al., "Eosiniophilic esophagitis in children and adults: A systematic review and consensus recommendations for diagnosis and treatment," Gastroenterology 2007; 133:1342-1363.
Garrett J K et al., "Anti-interleukin-5 (mepolizumab) therapy for hypereosinophilic syndromes," J. Allergy Clin. Immunol. 2004; 113:115-9.
Gliani, K. et al., "Aerosolisation properties of disodium cromoglycate microparticles spray dried from different water to ethanol ratio," JPP S6(Suppl.):Abstract 043 (2004).
Guajardo J R et al., "Eosinophil-associated gastrointestinal disorders: a world-wide-web based registry," J. Pediatr. 2002; 141:576-81.
Hardy, J.G. et al., "A Comparison of the Gastric Retention of a Sucralate Gel and a Sucralate Suspension," Eur. J. Pharm. Biopharm. 39(2):70-74 (1993).
Honkanen, O. et al., "Bioavailbility and in vitro oesophageal sticking tendency of hydroxypropyl methylcellulose capsul formulations and corresponding gelatine capsul formulations," Eur. J. Pharm. Sci. 15:479-488 (2002).
Ishibashi, H. et al., "Oral administration of itraconazole solution has superior efficacy in experimental oral and oesophageal candidiasis in mice than its intragastric administration," J. Antimicrobial Chemotherapy 59:317-320 (2007).

Kagalwalla A F et al., "Effect of six-food elimination diet on clinical and histologic outcomes in eosinophilic esophagitis," Clin. Gastroenterol. Hepatol. 2006; 4:1097-102.
Karnam, U. and Hirano, I., "Effectiveness of Oral Budesonide Suspension in Adult Patients with Eosinophilic Esophagitis," http://download.abstractcentral.com/ddw2008/myddw2008/S1974.html.
Kelly K J et al., "Eosinophilic esophagitis attributed to gastroesophageal reflux: improvement with an amino acid-based formula," Gastroenterology 1995; 109: 1503-12.
Laine, L. and Rabeneck, L., "Prospective study of fluconazole suspension for the treatment of oesophageal candidiasis in patients with AIDS," Ailment Pharmacol.Ther. 9:553-556 (1995).
Liacouras C A., "Eosinophilic esophagitis: treatment in 2005," Curr. Opin. Gastroenterol. 2006; 22:147-152.
Liacouras C A and Ruchelli E., "Eosinophilic esophagitis," Cuff. Opin. Pediatr. 2004; 16:560-6.
Liacouras C A et al., "Primary eosinophilic esophagitis in children: successful treatment with oral corticosteroids," J. Pediatr. Gastroenterol. Nutr. 1998; 26:380-5.
Liacouras C A et al., "Eosinophilic esophagitis: a 10-year experience in 381 children," Clin. Gastroenterol. Hepatol. 2005; 3:1198-206.
Markowitz J E et al., "Elemental diet is an effective treatment for eosinophilic esophagitis in children and adolescents," Am. J. Gastroenterol. 2003; 98:777-82.
Martins, M.D. and Rex, J.H., "Fluconazole Suspension for Oropharyngeal Candidiasis Unresponsive to Tablets," Annals Internal Med. 126(4):332-333 (1997).
Mishra A et al., "An etiological role for aeroallergens and eosinophils in experimental esophagitis," J. Clin. Invest. 2001; 107:83-90.
Mueller S et al., "Eosinophil infiltration and degranulation in oesophageal mucosa from adult patients with eosinophilic oesophagitis: a retrospective comparative study on pathologic biopsy," J. Clin. Pathol. 2006; 59:1175-80.
Newman, S.P. et al., "New developments in radionuclide imaging for assessing drug delivery in man," Eur. J. Pharma. Sci. 18:19-22 (2003).
Nicolazzo, JA et al., "Buccal penetration enhancers—how do they really work?" J. Controlled Release 2005; 105:1-15.
Noel R J et al., "Clinical and immunopathologic effects of swallowed fluticasone for eosinophilic esophagitis," Clin. Gastroenterol. Hepatol. 2004; 2:568-75.
Noel R J et al., "Eosinophilic esophagitis," N. Engl. J. Med. 2004; 351:940-1.
Oliviera, C. et al., "Eosinophilic esophagitis and intermediate esophagitis after tracheoesophageal fistula repair: a case series," J. Ped. Surg. 43:810-814 (2008).
Orenstein S R et al., "The spectrum of pediatric eosinophilic esophagitis beyond infancy: a clinical series of 30 children," Am. J. Gastroenterol. 2000; 95:1422-30.
Parfitt J R et al., "Eosinophilic esophagitis in adults: distinguishing features from gastroesophageal reflux disease: a study of 41 patients," Mod. Pathol. 2006; 19:90-6.
Plaza-Martin, AM et al., "Polysensitization to aeroallergens and food in eosinophilic esophagitis in a pediatric population," Alergol. Immunopathol. 2007; 35:35-7.
Potter J W et al., "Eosinophilic esophagitis in adults: an emerging problem with unique esophageal features," Gastrointest. Endosc. 2004; 59:355-61.
Potts, A.M. et al., "In vivo determination of the oesophageal retention of smart hydrogel," The 24$^{th}$ International Symposium on Controlled Release of Bioactive Materials, Stockholm Sweden, Jun. 15-19, 1997 #5058, pp. 335-336.
Ravelli A M et al., "Dilated Intercellular Spaces: A Major Morphological Feature of Esophagitis," J. Pediatr. Gastroenterol. Nutr. 2006; 42:510-515.
Remedios M et al., "Eosinophilic esophagitis in adults: clinical, endoscopic, histologic findings, and response to treatment with fluticasone propionate," Gastrointest. Endosc. 2006; 63:3-12.
Richardson, J.C. et al., "Oesophageal bioadhesion of sodium alginate suspensions: particle swelling and mucosal retention," Eur. J. Pharm. Sci. 23:49-56 (2004).
Rothenberg M E., Eosinophilic gastrointestinal disorders, J. Allergy Clin. Immunol. 2004; 113:11-28.

(56) References Cited

OTHER PUBLICATIONS

Rothenberg M E, et al., "Pathogenesis and clinical features of eosinophilic esophagitis," J. Allergy Clin. Immunol. 2001; 108:891-4.
Ruchelli E et al., "Severity of esophageal eosinophilia predicts response to conventional gastroesophageal reflux therapy," Pediatr. Dev. Pathol. 1999; 2:15-8.
Sant'Anna A M et al., "Eosinophilic Esophagitis in Children: Symptoms, Histology and pH Probe Results," J. Pediatr. Gastroenterol. Nutr. 2004; 39:373-377.
Shah, A. and Hirano, I., "Treatment of Eosinophilic Esophagitis: Drugs, Diet, or Dilation?" Curr. Gastroent. Reports 9:181-188 (2007).
Smart, J.D. et al., "The retention of $^{14}$C-labelled poly(acrylic acids) on gastric and oesaphageal mucosa: an in vitro study," Eur. J. Pharma. Sci. 20:83-90 (2003).
Spergel JM., "Eosinophilic esophagitis in adults and children: evidence for a food allergy component in many patients," Curr. Opin. Allergy Clin. Immunol. 2007; 7:274-8.
Spergel J M et al., "Treatment of eosinophilic esophagitis with specific food elimination diet directed by a combination of skin prick and patch tests," Ann. Allergy Asthma Immunol. 2005; 95:336-43.
Spergel J M et al., "The use of skin prick tests and patch tests to identify causative foods in eosinophilic esophagitis," J. Allergy Clin. Immunol. 2002; 109:363-8.
Steiner S J et al., "Correlation between number of eosinophils and reflux index on same day esophageal biopsy and 24 hour esophageal pH monitoring," Am. J. Gastroenterol. 2004; 99:801-5.
Steiner S J et al., "Severity of Basal Cell Hyperplasia Differs in Reflux Versus Eosinophilic Esophagitis," J. Pediatr. Gastroenterol. Nutr. 2006; 42:506-509.
Straumann A and Simon H U, "Eosinophilic esophagitis: escalating epidemiology?" J. Allergy Clin. Immunol. 2005; 115:418-9.
Straumann A et al., "Natural history of primary eosinophilic esophagitis: a follow-up of 30 adult patients for up to 11.5 years," Gastroenterology 2003; 125:1660-9.
Tang, M. et al., "Bioadhesive oesophageal bandages: protection against acid and pepsin injury," Int. J. Pharma. 292:169-177 (2005).
Teitelbaum J E et al., "Eosinophilic esophagitis in children: immunopathological analysis and response to fluticasone propionate," Gastroenterology 2002; 122:1216-25.
Varum, F.J.O. et al., "Mucoadhesion and the Gastrointestinal Tract," Critical Reviews Ther. Drug Carrier Systems 25(3):207-258 (2008).
Wise, J.L. et al., "Regional differences in oesophageal motor function," Neurogastroenterol. Motil 16:31-37 (2004).
Young, S.A. and Smart, J.D., "A novel in-vitro apparatus for evaluating the mucoadhesion of liquid and semi-solid formulations," J. Pharm. Pharmacol. 50(Suppl):167 (1998).
Blanchard et al., "Eotaxin-3 and a uniquely conserved gene-expression profile in eosinophilic esophagitis," J. Clin Invest., 116(2):536-547 (2006).
CN200880125118 Office action mailed Jun. 8, 2013.
CN200880125118 Office action mailed Feb. 7, 2013.
CN200880125118 Office action mailed Jun. 1, 2012.
CN200880125118 Office action mailed Oct. 10, 2011.
EP 08876449.3 Office Action dated Jun. 11, 2013.
EP 08848917.4 Extended European Search Report dated Aug. 26, 2013.
EP 08850126.7 Extended European Search Report dated Aug. 28, 2013.
EP 08848597.4 Extended European Search Report dated Aug. 26, 2013.
EP 11799004.4 Extended European Search Report dated Oct. 29, 2013.
Freers, "Maltodextrin," Handbook of Pharmaceutical Excipients, 5th edition, 2006: 442-444.
JP2010-533128 Office Action dated Jul. 23, 2013.
NDB No. 19868 (Exhibit A, 2007).
PCT/US2008/083290 IPRP dated Feb. 22, 2011.
Suarez et al., "Caustic esophagitis in children," Anales Espanoles de Pediatria, Mar. 1992, 36(3):205-207, Abstract, 1 page.
U.S. Appl. No. 11/595,513 Office Action mailed Feb. 6, 2012.
U.S. Appl. No. 11/595,513 Office Action mailed May 12, 2011.
U.S. Appl. No. 11/595,513 Office Action mailed Jan. 7, 2010.
U.S. Appl. No. 11/595,513 Office Action mailed Jun. 30, 2010.
U.S. Appl. No. 12/269,693 Office Action mailed Feb. 9, 2012.
U.S. Appl. No. 12/269,693 Office Action mailed Jul. 19, 2012.
U.S. Appl. No. 12/269,693 Office Action mailed Jun. 1, 2011.
U.S. Appl. No. 12/762,222 Office Action mailed Aug. 8, 2012.
U.S. Appl. No. 12/762,222 Office Action mailed Mar. 13, 2013.
U.S. Appl. No. 12/762,222 Office Action mailed May 16, 2013.
U.S. Appl. No. 12/269,572 Office Action mailed Dec. 21, 2012.
U.S. Appl. No. 12/269,572 Office Action mailed Jun. 7, 2012.
U.S. Appl. No. 12/269,572 Office Action mailed Mar. 5, 2010.
U.S. Appl. No. 12/269,572 Office Action mailed Oct. 12, 2011.
U.S. Appl. No. 12/269,572 Office Action mailed Oct. 25, 2010.
U.S. Appl. No. 12/269,740 Office Action mailed Jun. 8, 2011.
U.S. Appl. No. 12/269,740 Office Action mailed Nov. 17, 2010.
U.S. Appl. No. 12/269,816 Office Action mailed Apr. 10, 2012.
U.S. Appl. No. 12/269,816 Office Action mailed Feb. 7, 2011.
U.S. Appl. No. 12/269,816 Office Action mailed Mar. 19, 2013.
U.S. Appl. No. 12/269,816 Office Action mailed Nov. 8, 2012.
U.S. Appl. No. 12/269,816 Office Action mailed Sep. 8, 2011.
U.S. Appl. No. 12/269,816 Office Action mailed Oct. 24, 2013.
U.S. Appl. No. 12/269,821 Office Action mailed Apr. 26, 2011.
U.S. Appl. No. 12/269,832 Office Action mailed May 4, 2011.
U.S. Appl. No. 12/426,858 Office Action mailed Jun. 1, 2011.
U.S. Appl. No. 12/814,335 Office Action mailed Dec. 21, 2011.
U.S. Appl. No. 12/814,335 Office Action mailed Jul. 17, 2012.
U.S. Appl. No. 13/168,601 Office Action mailed Apr. 9, 2013.
U.S. Appl. No. 13/168,601 Office Action mailed Jul. 3, 2012.
web page: www.scientificpsychic.com/blogentries/splenda-sweetener-the-delusion-of-low-calories.html, 2007.
U.S. Appl. No. 12/762,222 Office Action mailed Dec. 4, 2013.
PCT/US2008/012712 International Preliminary Report on Patentability dated May 18, 2010.
PCT/US2008/012780 International Preliminary Report on Patentability dated May 18, 2010.
PCT/US2008/012781 International Preliminary Report on Patentability dated May 18, 2010.
PCT/US2008/012783 International Preliminary Report on Patentability dated May 18, 2010.
PCT/US2009/041316 International Preliminary Report on Patentability dated Oct. 26, 2010.
PCT/US2010/038411 International Preliminary Report on Patentability dated Dec. 12, 2011.
PCT/US2011/041871 International Preliminary Report on Patentability dated Dec. 2, 2012.
EP 10786942.2 Search Report dated Jan. 8, 2014.

* cited by examiner

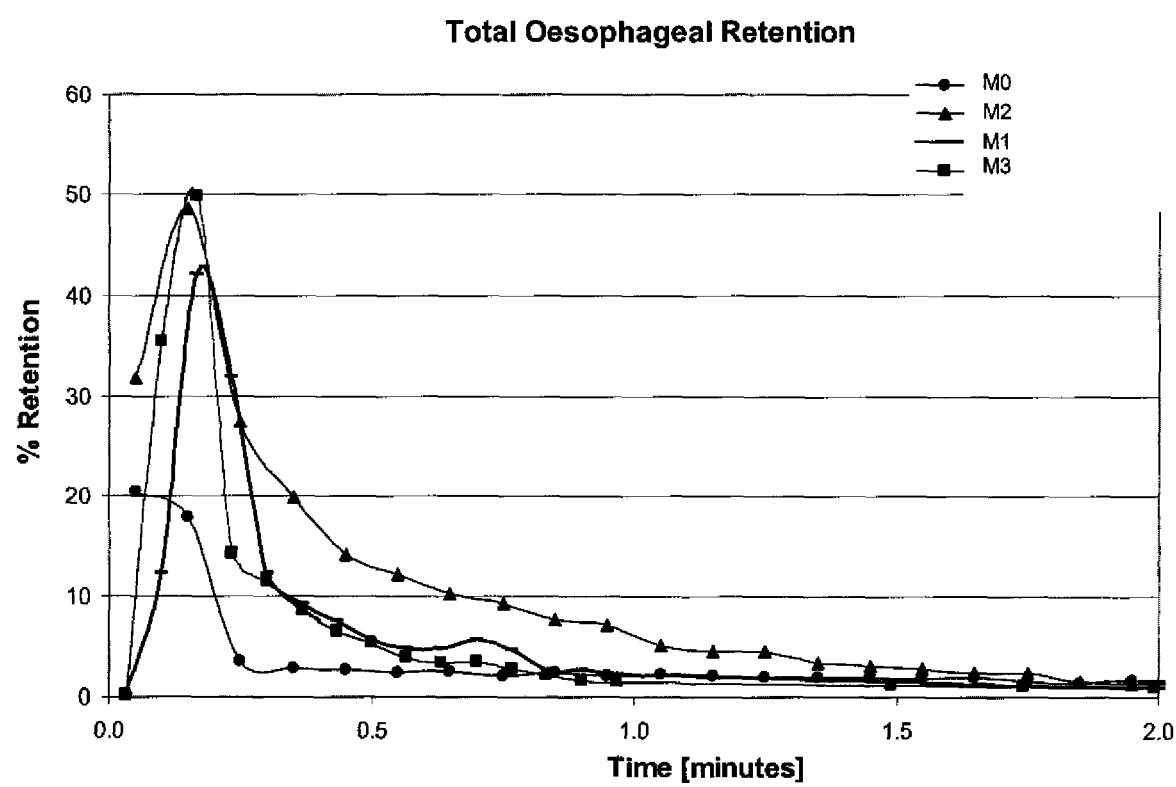

COMPOSITIONS FOR THE TREATMENT OF GASTROINTESTINAL INFLAMMATION

CROSS-REFERENCE

This application claims the benefit of U.S. Provisional Application No. 60/987,720, filed Nov. 13, 2007; U.S. Provisional Application No. 61/012,012, filed Dec. 6, 2007; U.S. Provisional Application No. 61/015,998, filed Dec. 21, 2007; U.S. Provisional Application No. 61/019,818, filed Jan. 8, 2008; U.S. Provisional Application No. 61/034,941, filed Mar. 7, 2008; U.S. Provisional Application No. 61/035,348, filed Mar. 10, 2008; U.S. Provisional Application No. 61/054,103, filed May 16, 2008; U.S. Provisional Application No. 61/054,104, filed May 16, 2008; U.S. Provisional Application No. 61/054,105, filed May 16, 2008; U.S. Provisional Application No. 61/054,106, filed May 16, 2008; U.S. Provisional Application No. 61/054,107, filed May 16, 2008; and U.S. Provisional Application No. 61/090,568, filed Aug. 20, 2008, which applications are incorporated herein by reference.

BACKGROUND OF THE INVENTION

Esophageal inflammation disorders are gaining increased recognition in both adults and children. One example is eosinophilic esophagitis (EE or EoE), which is an emerging, and fast-growing disorder characterized by high levels of eosinophils in the esophagus, as well as basal zone hyperplasia. EE (EoE) is thought to be provoked, in at least a subset of patients, by food allergies or airborne allergen exposure (1-5, 44). EE (EoE) diagnosis is often associated with other hypersensitivity disorders, including asthma, rhinitis, and other food and aeroallergen inhalant sensitivities (39-40). Diagnosis is often made, e.g., in young children and depends on the finding of 15 to 20 or more to 24 or more eosinophils per high power field (eos/hpf) within esophageal mucosal biopsies (6-12).

In parallel with other atopic disorders, the incidence of FE (EoE) appears to be increasing (15, 35). The disorder may present with reflux-like symptoms, pain and dysphagia, clinical symptoms similar to the presentation of gastroesophageal reflux disease ("GERD") (42). Symptoms of EE (EoE) include, for example, abdominal pain, chest pain, choking, difficulty swallowing, failure to thrive, nausea, reflux not relieved by standard anti-flux therapy, skin rash or hives, vomiting, and weight loss. In one series, 15% of EE (EoE) patients had concurrent developmental delay (45).

Although EE (EoE) is becoming more frequently diagnosed throughout developing countries (7, 8, 13-16) many aspects of the disease remain unclear including its etiology, natural history and optimal therapy. Symptoms of EE (EoE) often mimic those of GERD and include vomiting, dysphagia, pain and food impaction (8, 14, 17-20). However, treatment of EE (EoE) and GERD differ and it is important to distinguish between them, particularly as untreated EE (EoE) may be associated with esophageal narrowing in 10-30% of cases (14, 18, 20, 21). The overlap of GERD and EE (EoE) symptoms is common; failure to respond to high PPI GERD treatment may be one diagnostic guideline for EE (EoE) (42). The common occurrence regarding misdiagnosis of EE (EoE) for GERD often results in delayed treatment for patients with EE. (42).

Long term systemic steroid therapy can result in significant secondary side effects on growth and bone development. Although treatment with anti-IL-5 monoclonal antibody has been reported to be successful in EE, this therapy is currently not approved for use in children (36).

Current treatments include elimination diets (22, 23), and elemental formulas (2, 24). Identifying true inciting food allergens can be difficult and elemental formulas are often unpalatable, thereby making dietary interventions complicated (1, 22). Improvised puff and swallow techniques may be difficult for patients, especially smaller children, and especially children with developmental delays, to perform efficiently. This may result in a less than effective dose of a topical steroid being delivered to the esophagus.

SUMMARY OF THE INVENTION

Provided in certain embodiments herein is an oral pharmaceutical composition comprising a corticosteroid, and a mucoadhesive agent. In specific embodiments, the oral pharmaceutical composition is a stable oral pharmaceutical composition, being both chemically and physically stable for at least one month (e.g., under ambient conditions, or under inert conditions, such as under an inert gas or vacuum). In some embodiments, the oral pharmaceutical composition further comprises a liquid vehicle. In certain embodiments, the corticosteroid is a topically active corticosteroid. In some embodiments, the corticosteroid is budesonide. In other embodiments, the corticosteroid is fluticasone propionate.

In some embodiments, when an oral pharmaceutical composition described herein is administered to an esophagus, e.g., by oral administration, at least 50%, 20%, 10%, 9%, 8%, 7%, 6%, 5%, 4%, 3%, 2%, or 1% of the oral pharmaceutical composition adheres to or resides upon the esophagus for at least 15 seconds, or 1 minute. In certain embodiments, when an oral pharmaceutical composition described herein is administered to the esophagus, e.g., by oral administration, at least 50%, 20%, 10%, 9%, 8%, 7%, 6%, 5%, 4%, 3%, 2%, or 1% of the corticosteroid adheres to or resides upon the esophagus for at least 15 seconds, or at least 1 minute. In some embodiments, at least 50%, 20%, 10%, 9%, 8%, 7%, 6%, 5%, 4%, 3%, 2%, or 1% of the corticosteroid adheres to or is absorbed by the esophagus at least 15 seconds, or at least 1 minute after application of an oral pharmaceutical composition described herein is administered to the esophagus, e.g., by oral administration. In certain embodiments, administration of the oral pharmaceutical composition to the esophagus includes orally administering and/or swallowing at least part of the oral pharmaceutical composition or dose of the oral pharmaceutical composition.

In certain embodiments, the weight percent of an oral pharmaceutical composition described herein that adheres to or resides upon the esophagus 15 seconds or 1 minute after application to the esophagus, e.g., by oral administration, is greater than the weight percent of a control composition that adheres to or resides upon the esophagus 15 seconds or 1 minute after application to the esophagus of the control composition, e.g., by oral administration. In some embodiments, the amount of corticosteroid that adheres to or resides upon the esophagus 15 seconds or 1 minute after application to the esophagus, e.g., by oral administration, of an oral pharmaceutical composition described herein is greater than the amount of corticosteroid that adheres to or is absorbed by the esophagus 15 seconds or 1 minute after application to the esophagus, e.g., by oral administration, of a control composition. In some embodiments, the amount of corticosteroid that adheres to or is absorbed by the esophagus 15 seconds or 1 minute after application to the esophagus, e.g., by oral administration, of an oral pharmaceutical composition described herein is greater than the amount of corticosteroid that adheres to or is absorbed by the esophagus 15 seconds or 1 minute after application to the esophagus, e.g., by oral administration of a control composition. In specific embodiments, a control composition described herein comprises the same corticosteroid in the same amount as present in the oral pharmaceutical composition, and comprises about 4 mL of an aqueous formulation (e.g., a Pulmicort® formulation) and 10 packs of Splenda® (distributed by McNeil Nutritionals, LLC Fort Washington, Pa. 19034-2299) for every 0.5 mg of corticosteroid.

In certain embodiments, the mucoadhesive agent described herein is, by way of non-limiting example, a mucoadhesive polysaccharide, a carbopol. Carbopols include, by way of non-limiting example, a cross-linked acrylic acid polymer, Carbopol Ultrez and Carbopol 974P. In some embodiments, the mucoadhesive agent described herein is, by way of non-limiting example an alginate. In specific embodiments, the alginate is, by way of non-limiting example, sodium alginate LF120 and/or sodium alginate H120L. In certain embodiments, the mucoadhesive agent comprises one or more maltodextrin. In specific embodiments, the maltodextrin does not substantially increase the viscosity of the oral pharmaceutical composition (e.g., compared to an otherwise identical composition lacking the maltodextrin). In further or alternative embodiments, the maltodextrin is chosen for its mucoadhesive properties (e.g., its ability to impart mucoadhesive character upon the oral pharmaceutical composition). In some embodiments, the oral pharmaceutical composition comprises a second maltodextrin that increases the viscosity of the oral pharmaceutical composition (e.g., compared to an otherwise identical composition lacking the second maltodextrin). In specific embodiments, the second maltodextrin does not substantially affect the mucoadhesive characteristic of the pharmaceutical composition (e.g., compared to an otherwise identical composition lacking the second maltodextrin).

In some embodiments, a mucoadhesive agent utilized in an oral pharmaceutical composition disclosed herein imparts an increased viscosity upon the oral pharmaceutical composition (e.g., compared to an otherwise identical composition lacking the mucoadhesive agent). In other embodiments, the mucoadhesive agent does not substantially increase the viscosity of the oral pharmaceutical composition (e.g., compared to an otherwise identical composition lacking the mucoadhesive agent).

In certain embodiments, an oral pharmaceutical composition described herein further comprises a second mucoadhesive agent. In further or alternative embodiments, an oral pharmaceutical composition described herein further comprises a viscosity enhancing agent.

Also provided herein is a method of treating, preventing or alleviating gastrointestinal inflammation or symptoms of gastrointestinal inflammation in an individual comprising orally administering to said individual any pharmaceutical composition described herein. In certain embodiments, the gastrointestinal inflammation is, by way of non-limiting example, esophageal inflammation. In specific embodiments, the individual has been diagnosed with eosinophilic esophagitis, an inflammatory bowel disease involving the esophagus, Crohn's disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., *Candida*, turolopsis, histoplasma *Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, or gastro enteritis. In more specific embodiments, the individual has eosinophilic esophagitis. In other specific embodiments, individual has been diagnosed with gastroesophageal reflux disease (GERD), nonerosive reflux disease (NERD), or erosive esophagitis. In some embodiments, the gastrointestinal inflammation is, by way of non-limiting example, inflammation of the stomach and/or the small intestines, e.g., gastro enteritis.

In certain embodiments, a pharmaceutical composition described comprises or a method described herein comprises administering (e.g., per day or per dose) to an individual about 0.1 mg to about 20 mg corticosteroid, about 0.1 mg to about 10 mg corticosteroid, about 0.3 mg to about 5 mg corticosteroid, about 0.3 mg to about 4 mg corticosteroid, about 1 to about 2 mg corticosteroid, about 2 to about 3 mg corticosteroid, or about 0.25 to about 2.5 mg of corticosteroid.

In some embodiments, a method described herein comprises administering a composition described herein to a child. In specific embodiments, the child less than 19 years old, less than 16 years old, less than 12 years old, less than 8 years old, less than 6 years old, less than 4 years old or less than 2 years old. In some embodiments, a method described herein comprises administering a composition described herein to an adult.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the percent amount of composition present in the esophagus as a function of time following oral administration (by measuring the amount of radiolabel present in the esophagus).

DETAILED DESCRIPTION OF THE INVENTION

In certain embodiments, the present invention is directed to methods and pharmaceutical compositions for treating, preventing or alleviating the symptoms of and inflammation associated with inflammatory diseases involving the gastrointestinal tract, including the esophagus, stomach and/or digestive tract. Provided herein are methods of treating, preventing or alleviating, for example, esophageal inflammation in an individual. In certain embodiments, these methods comprise orally administering to said individual a corticosteroid in association with at least one excipient to increase the mucoadhesive characteristic of the composition (a mucoadhesive agent). In some embodiments, provided herein is an pharmaceutical composition comprising a corticosteroid and a mucoadhesive agent. In certain embodiments, the pharmaceutical composition further comprises a liquid vehicle. In further or alternative embodiments, the pharmaceutical composition is suitable for oral administration. In some embodiments, the increased mucoadhesive characteristic of the composition allows the composition to be in contact with the esophagus for an extended period of time following administration.

In certain embodiments, the excipient or excipients chosen increase the interaction of the composition with the surface of the gastrointestinal tract (e.g., the mucosa and/or epithelium of the gastrointestinal tract or of a specific site of the gastrointestinal tract, such as the esophagus) by at least 1.02 fold, by at least 1.05-fold, by at least 1.1 fold, by at least 1.2 fold, by at least 1.25-fold, by at least 1.5-fold, by at least 2-fold, by at least 3-fold, by at least 4-fold or by at least 5-fold. In certain embodiments, the increased interaction of the composition is an at least 1.02 fold, by at least 1.05-fold, by at least 1.1 fold, by at least 1.2 fold, by at least 1.25-fold, by at least 1.5-fold, by at least 2-fold, by at least 3-fold, by at least 4-fold or by at least 5-fold of interaction of the composition with the esophagus that occurs following passing of the bolus of the composition being swallowed. In certain embodiments, these increases are measured and compared to the measure of an otherwise similar composition lacking the excipient or excipients that increase the interaction of the composition with the surface of the gastrointestinal tract. In certain instances, increased interaction of the composition is measured as a function of the amount of composition present in a selected or targeted portion of the gastrointestinal tract, such as the esophagus (e.g., as measured after the bolus has passed through the esophagus, which may be 5 seconds, 6 seconds, 7 seconds, 8 seconds, 9 seconds, 10 seconds, 11 seconds, 12 seconds, 13 seconds, 14 seconds, 15 seconds, or the like following initial swallowing of at least a portion of the composition). In specific instances, the amount of composition present in the esophagus is measured in any suitable manner, e.g., by radiolabeling the composition and measuring the amount of the composition in the esophagus utilizing gamma scintigraphy. An increase in the interaction of the composition with the surface of the gastrointestinal tract (e.g., the surface of the esophagus) may be measured by measuring the retention time of the material along a length of a surface of the gastrointestinal tract (e.g., the surface of the esophagus), wherein the retention time is increased in the presence of the excipients as compared to its absence. In another embodiment an increased interaction may be measured by the decrease in physiological manifestations or symptoms of the disease or ailment to be treated, including a decrease in total eosinophil counts in a target sample.

In one aspect of the invention, the use of the excipients may act to decrease the quantity of active agents needed to elicit a response in the absence of the excipients. In some embodiments, the excipients may decrease the amount of corticosteroid used. Accordingly, the compositions provided herein may provide an additional advantage of decreasing the amount of active agent needed to treat subjects afflicted with inflammatory diseases involving the gastrointestinal tract, including the esophagus, stomach and/or digestive tract.

In certain embodiments, an active is utilized in an pharmaceutical composition described herein that would benefit from an increased interaction with a surface of the gastrointestinal tract (e.g., a topically active corticosteroid).

An individual suitable for treatment with the compositions disclosed herein may, for example, have been diagnosed with a disease or condition including, but not limited to, eosinophilic esophagitis, inflammatory bowel diseases involving the esophagus, eosinophilic gastroenteritis, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., *Candida*, turolopsis, histoplasma *Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, or gastro enteritis. The composition may also be used in treating other gastrointestinal disorders, including stomach and duodenal ulcers, hyperactive acidic discharge disorders, such as Zollinger-Ellison syndrome and laryngeal disorders.

An individual suitable for treatment with the compositions disclosed herein may, for example, have been diagnosed with a disease or condition including, but not limited to, eosinophilic esophagitis, inflammatory bowel diseases involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., *Candida*, turolopsis, histoplasma *Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, eosinophilic gastric outlet obstruction and related inflammation, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, or gastro enteritis. The composition may also be used in treating individuals diagnosed with other gastrointestinal disorders, including stomach and duodenal ulcers, hyperactive acidic discharge disorders, such as Zollinger-Ellison syndrome and laryngeal disorders. In some embodiments, the compositions or methods disclosed herein are used in methods of treating individuals diagnosed with other gastrointestinal disorders, including, by way of non-limiting example, Barrett's Esophagus, gastroesophageal reflux disease (GERD), nonerosive reflux disease (NERD), or erosive esophagitis. In some embodiments, the methods of treating, preventing or alleviating inflammation or symptoms of inflammation include methods of treating any of the gastrointestinal disorders described herein. In certain embodiments, these methods comprise orally administering to said individual a corticosteroid-containing compositions described herein.

Provided herein are methods for treating, preventing and alleviating any chronic inflammatory or malignant state that involves the gastrointestinal tract, such as the esophagus, and responds to steroid therapy. The methods and compositions of the present invention are useful, for example, for treating, preventing and alleviating inflammation and/or symptoms and associated with eosinophilic esophagitis, inflammatory bowel diseases involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., *Candida*, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, Epidermolysis bullosa, post-surgery inflammation, and gastro enteritis. The present methods are also useful for treating, preventing or alleviating symptoms and/or inflammation associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application. As used herein, inflammation and/or symptoms associated with a disorder or disease disclosed herein includes inflammation and/or symptoms associated with, caused by and/or resulting from the disorder or disease.

As used herein, unless otherwise stated, the use of the terms "a", "an" and "the" include both singular and multiple embodiments. As used herein, the term "individual" includes any animal. In some embodiments, the animal is a mammal. In certain embodiments, the mammal is a human. In specific embodiments, the human is an adult. In other embodiments, the human is a child (e.g., a child under 12 or a child under 6). In certain embodiments, the human is an infant. As used herein, the phrase "method of treating" or "method for treating" can, in some embodiments, encompass methods of preventing, reducing the incidences of, providing prophylactic treatment, treating and alleviating. As used herein, the phrase "an effective amount" and "a therapeutically effective amount" is an amount sufficient to elicit a change in the symptoms of or inflammation associated with gastrointestinal disorders, including but not limited to esophageal inflammation, eosinophilic esophagitis, GERD, NERD, or erosive esophagitis. As used herein, the term "or" includes "and" and "or".

As used herein, the phrase "treating inflammatory diseases involving the esophagus" includes treating symptoms of such diseases and treating inflammation associated with the diseases.

In certain embodiments, as used herein, "substantially" increasing or affecting includes increasing or deviating, respectively, in an amount of, by way of non-limiting example, about 10%, 5%, 3%, 2%, or 1%.

Methods and Compositions

In certain embodiments, the corticosteroids used in the present invention include topical steroids including, for example, budesonide or fluticasone propionate. In some embodiments, corticosteroids are selected from, by way of non-limiting example, aclometasone, amcinomide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fuprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, remexolone, tixocortol, triamcinolone and ulobetasol, and combinations, pharmaceutically acceptable salts and esters thereof. In a specific embodiment, the corticosteroid is budesonide. In another embodiment, the corticosteroid is an ester of fluticasone, e.g., fluticasone propionate.

Provided herein are methods and pharmaceutical compositions for treating, preventing or alleviating the symptoms of, and inflammation associated with, inflammatory diseases of the gastrointestinal tract, including but not limited to the upper gastrointestinal tract (e.g., the esophagus). Also provided herein are methods and pharmaceutical compositions for preventing or alleviating the symptoms of gastrointestinal reflux and an increase in gastric pH, which are associated with inflammatory diseases of the gastrointestinal tract, including but not limited to the esophagus.

In certain embodiments, a corticosteroid (e.g., budesonide or fluticasone propionate) that is administered in oral form, in a formulation with increased mucoadhesive characteristic, is delivered to, e.g., the esophagus in an effective dose to reduce the inflammation of the esophagus.

In one aspect, provided herein is an oral pharmaceutical composition comprising a corticosteroid and a mucoadhesive agent. In various aspects, an exemplary corticosteroid is budesonide, 16,17-(butylidenebis(oxy))-11,21-dihydroxy-, (11-β,16-α)-pregna-1,4-diene-3,20-dione, or fluticasone propionate, S-(fluoromethyl)6α,9-difluoro-11β-17-dihydroxy-16α-methyl-3-oxoandrosta-1,4-diene-17β-carbothioate, 17 propionate or (6α,11β,16α,17β)-6,9-Difluoro-11-hydroxy-16-methyl-3-oxo-17-(1-oxopropoxy)androsta-1,4-diene-17-carbothioic acid S-(fluoromethyl)ester.

In certain embodiments, pharmaceutical compositions disclosed herein and used herein comprise one or more excipients. Excipients useful herein include, by way of non-limiting example, mucoadhesive agents, viscosity enhancing agents, binders, fillers, lubricants, solvents, suspension agents, flavoring agents, coloring agents, sweeteners, preservatives, antioxidants, buffering agents, humectants, chelating agents, surfactants, and the like.

In certain embodiments, the corticosteroid(s) utilized herein are utilized as particles (e.g., corticosteroid particles suspended or dispersed in an aqueous medium). In specific embodiments, the particles are microparticles. In some embodiments, the microparticles have a mean diameter of about 0.1 microns to about 50 microns. In specific embodiments, the microparticles have a mean diameter of about 1 micron to about 20 microns. In certain embodiments, at least 95%, at least 98%, or at least 99% of the microparticles have a diameter of less than 10 microns.

In some embodiments, a composition or formulation described herein comprises less than 50% w/w, less than 40% w/w, less than 30% w/w, less than 20% w/w, less than 10% w/w, less than 8% w/w, less than 6% w/w, less than 5% w/w, less than 4% w/w, less than 3% w/w, less than 2% w/w, or about 2% w/w, less than 1% w/w, less than 0.5% w/w, less than 0.3% w/w, less than 0.2% w/w, or about 0.2% w/w of undissolved particles. In certain embodiments, a composition or formulation described herein is substantially free of non-corticosteroid particles.

In some embodiments, the active corticosteroid described herein is substituted with another active agent. In certain embodiments, the active agent is a therapeutic agent that targets the esophagus, e.g., for treating inflammation of the esophagus, mucusitis, cancer of the esophagus, infections (e.g., bacterial or fungal infections) of the esophagus, esophageal wounds and/or contusions, or the like. In some embodiments, the active agent is a therapeutic agent that is systemically absorbed through the esophagus. In specific embodiments, the therapeutic agent that is systemically absorbed through the esophagus is an agent that is degraded or loses its efficacy in some when in the stomach, e.g., a therapeutic peptide.

Mucoadhesive agents to be used herein include, by way of non-limiting example, a soluble polyvinylpyrrolidone polymer (PVP), a carbopol, a crosslinked poly(acrylic acid) (e.g., Carbopol 974P), a carbomer homopolymer, a carbomer copolymer, a water-swellable, but water-insoluble, fibrous, cross-linked carboxy-functional polymer, a mucoadhesive polysaccharide (e.g., a hydrophilic polysaccharide gum), one or more maltodextrin, alginate, a cross-linked alginate gum gel, a water-dispersible polycarboxylated vinyl polymer. In some embodiments, the mucoadhesive agent is a carbopol. In a specific embodiment, the mucoadhesive agent is selected from, by way of non-limiting example, Carbopol 974P, Carbopol Ultrez 10, sodium alginate LF120 and sodium alginate H120L. As used herein, a mucoadhesive agent is an agent that adheres to a gastrointestinal surface (e.g., either or both of a gastrointestinal epithelia or mucosa). In some embodiments, the mucoadhesive agent is a cellulose. In specific embodiments, the mucoadhesive agent is a carboxymethyl-cellulose (CMC), e.g., sodium carboxymethyl-cellulose (NaCMC), microcrystalline cellulose (MCC), or a combination thereof. In one non-limiting example, the mucoadhesive agent is a combination of MCC and CMC (e.g., Avicel RC-591). In some embodiments, the CMC/MCC combination (e.g., Avicel® RC-591) is present in the composition in an amount of about 1 mg/mL to about 150 mg/mL, 1 mg/mL to about 75 mg/mL, or about 5 mg/mL to about 40 mg/mL. In certain embodiments, the CMC/MCC mixed weight ratio is between about 1/99 and about 99/1, about 20/80 and about 5/95, or about 15/85 and about 10/90. In a specific embodiment, the CMC is NaCMC and the CMC/MCC mixed weight ratio is about 11/89.

In specific embodiments, provided herein is a composition comprising both a CMC (e.g., a CMC/MCC mixture) and maltodextrin. In certain embodiments, the combination of a CMC (e.g., a CMC/MCC mixture) and maltodextrin provide an increased residence time on an afflicted or targeted surface of the gastrointestinal tract (e.g., esophagus), when compared to a composition having a similar amount of either the CMC (e.g., a CMC/MCC mixture) or maltodextrin alone.

In certain embodiments, the mucoadhesive agent comprises one or more maltodextrin. In various aspects, the physical characteristics of maltodextrins vary depending, e.g., on the dextrose equivalent of the specific maltodextrin. In certain aspects, the dextrose equivalent of a specific maltodextrin may affect the viscosity, hygroscopicity, sweetness, humectancy, plasticity, solubility and or mucoadhesiveness of the maltodextrin. Thus, in various embodiments, a maltodextrin is selected based on the specific character that is desired to be imparted upon the pharmaceutical composition described herein. In certain embodiments, a maltodextrin is selected that increases the mucoadhesive character of a composition described herein without substantially increasing the viscosity of the composition (e.g., compared to an otherwise identical composition lacking the maltodextrin). In some embodiments, the oral pharmaceutical composition comprises a second maltodextrin that increases the viscosity of the oral pharmaceutical composition (e.g., compared to an otherwise identical composition lacking the second maltodextrin). In specific embodiments, the second maltodextrin that does not substantially affect the mucoadhesive characteristic of the pharmaceutical composition (e.g., compared to an otherwise identical composition lacking the second maltodextrin).

In some embodiments, the mucoadhesive agent does not substantially increase the viscosity of the oral pharmaceutical composition (e.g., compared to an otherwise identical composition lacking the mucoadhesive agent). In further or alternative embodiments, the mucoadhesive agent is chosen for its mucoadhesive properties (e.g., its ability to impart mucoadhesive character upon the oral pharmaceutical composition).

In some embodiments, a mucoadhesive agent utilized in an oral pharmaceutical composition described herein imparts an increased viscosity upon the oral pharmaceutical composition (e.g., compared to an otherwise identical composition lacking the mucoadhesive agent). In other embodiments, the mucoadhesive agent does not substantially increase the viscosity of the oral pharmaceutical composition (e.g., compared to an otherwise identical composition lacking the mucoadhesive agent).

In some embodiments, at least one mucoadhesive agent is chosen for and used in the pharmaceutical composition so the addition of the at least one mucoadhesive agent does not substantially increase the viscosity of the resulting oral pharmaceutical composition (e.g., compared to an otherwise identical composition lacking the mucoadhesive agent).

In some embodiments, at least two mucoadhesive agents are chosen for and used in the pharmaceutical composition so the addition of the at least two mucoadhesive agents do not substantially increase the viscosity of the resulting oral pharmaceutical composition (e.g., compared to an otherwise identical composition lacking the mucoadhesive agents). In some embodiments, at least one mucoadhesive agent, if taken alone in the pharmaceutical composition would increase the viscosity of the pharmaceutical composition, but taken together with all components in the pharmaceutical composition, does not substantially increase the viscosity of the resulting oral pharmaceutical composition (e.g., compared to an otherwise identical composition lacking the at least one mucoadhesive agent).

In some embodiments, the viscosity of the composition is at least about 2 centipoise (cP), at least about 5 cP, at least about 10 cP, at least about 20 cP, at least about 25 cP, at least about 35 cP, at least about 40 cP, at least about 50 cP, at least about 200 cP, or at least about 225 cP. In some embodiments, the viscosity of the composition is at least about 100 cP. In certain embodiments, the viscosity of the composition, measured at 25 degrees Celsius, is about 50 cP to about 250,000 cP, about 50 cP to about 70,000 cP, about 50 cP to about 25,000 cP, about 50 cP to about 10,000 cP, about 50 cP to about 3,000 cP, or about 50 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition may range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g., as measured with a Brookfield viscometer at 25 degrees Celsius equipped with an ultra low adapter).

In some embodiments, the viscosity of the composition is measured at room temperature (about 25 degrees C.) with a shear rate of about 13.2 $sec^{-1}$. In certain embodiments, provided herein is a composition having a viscosity under such conditions that is at least about 2 centipoise (cP), at least about 5 cP, at least about 10 cP, at least about 20 cP, at least about 25 cP, at least about 30 cP, at least about 35 cP, at least about 40 cP, at least about 50 cP, at least about 200 cP, at least about 225 cP, at least about 250 cP, at least about 300 cP, or at least about 400 cP. In some embodiments, the viscosity of the composition under such conditions is about 50 cP to about 250,000 cP, about 50 cP to about 70,000 cP, about 50 cP to about 25,000 cP, about 50 cP to about 10,000 cP, about 50 cP to about 3,000 cP, about 50 cP to about 2,000 cP, about 250 cP to about 250,000 cP, about 250 cP to about 70,000 cP, about 250 cP to about 25,000 cP, about 250 cP to about 10,000 cP, about 250 cP to about 3,000 cP, or about 250 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition under such conditions may range from about 100 cP to about 200 cP, about 200 cP to about 300 cP, about 250 cP to about 600 cP or about 400 cP to about 600 cP. In specific embodiments, the viscosity of the formulation measured under such conditions is about 30 cP, about 40 cP, about 100 cP, about 200 cP, about 300 cP, about 400 cP, about 500 cP, or about 250,000 cP.

In some embodiments, the viscosity of the composition is measured at room temperature (about 25 degrees C.) with a shear rate of about 15 $sec^{-1}$ (e.g., with a gap between the spindle and the sample chamber wall of about 6 mm or greater). In certain embodiments, provided herein is a composition having a viscosity under such conditions that is at least about 150 centipoise (cP), at least about 160 cP, at least about 170 cP, at least about 180 cP, at least about 190 cP, or at least about 200 cP. In some embodiments, the viscosity of the composition under such conditions is about 150 cP to about 250,000 cP, 160 cP to about 250,000 cP, 170 cP to about 250,000 cP, 180 cP to about 250,000 cP, or 190 cP to about 250,000 cP.

In specific embodiments, the mucoadhesive agent used in any composition described herein is or comprises at least one maltodextrin.

In certain embodiments, a mucoadhesive agent (e.g., maltodextrin) is substantially or at least partially dissolved in a liquid vehicle. In some embodiments, an oral pharmaceutical composition described herein comprises less than about 0.1 g or less than about 1 g of maltodextrin for every mL of liquid vehicle in the oral pharmaceutical composition. In certain instances, a composition or formulation described herein comprises less than 2 g of maltodextrin/mL of composition, less than 1.5 g of maltodextrin/mL of composition, less than 1 g of maltodextrin/mL of composition, less than 0.5 g of maltodextrin/mL of composition, less than 0.25 g/mL of maltodextrin/mL of composition, about 0.05 g of maltodextrin/mL of composition to about 0.5 g of maltodextrin/L of composition, about 0.05 g of maltodextrin/mL of composition to about 0.4 g of maltodextrin/mL of composition, about 0.05 g of maltodextrin/mL of composition to about 0.3 g of maltodextrin/mL of composition, about 0.1 g of maltodextrin/mL of composition to about 0.5 g of maltodextrin/mL of composition, about 0.1 g of maltodextrin/mL of composition to about 0.4 g of maltodextrin/mL of composition, about 0.1 g of maltodextrin/mL of composition to about 0.3 g of maltodextrin/mL of composition, about 0.2 g of maltodextrin/mL of composition to about 0.5 g of maltodextrin/mL of composition, about 0.2 g of maltodextrin/mL of composition to about 0.4 g of maltodextrin/mL of composition, or about 0.2 g of maltodextrin/mL of composition to about 0.3 g of maltodextrin/ml of composition. In some embodiments, the maltodextrin is substantially dissolved in the liquid vehicle. In certain embodiments, the maltodextrin has a dextrose equivalents (DE) of greater than 4, greater than 5, greater than 10, greater than 11, greater than 12, greater than 13, greater than 14, greater than 15, about 15, about 4 to about 10, about 4 to about 9, about 4 to about 8, about 11 to about 20, about 12 to about 19, about 13 to about 18, or about 14 to about 16. In specific embodiments, the first maltodextrin has a DE of about 4 to about 10, about 4 to about 9, or about 4 to about 8 and the second maltodextrin has a DE of about 10 to about 20, about 12 to about 19, or about 13 to about 18. In some embodiments, at least one maltodextrin utilized in a composition described herein has a molecular weight high enough to increase the solubility of a corticosteroid, or to increase the suspendability of a corticosteroid particle.

In some embodiments, mucoadhesive agents are described, for example, in U.S. Pat. Nos. 6,638,521, 6,562, 363, 6,509,028, 6,348,502, 6,306,789, 5,814,330, and 4,900, 552, each of which is hereby incorporated by reference in its entirety.

In one non-limiting example, a mucoadhesive agent can be, by way of non-limiting example, at least two particulate components selected from titanium dioxide, silicon dioxide, and clay. In some embodiments, when the composition is not further diluted with any liquid prior to administration, the level of silicon dioxide is from about 3% to about 15%, by weight of the composition. In certain embodiments, silicon dioxide is selected from, by way of non-limiting example, fumed silicon dioxide, precipitated silicon dioxide, coacervated silicon dioxide, gel silicon dioxide, and mixtures thereof. In some embodiments, clay is selected from, by way of non-limiting example, kaolin minerals, serpentine minerals, smectites, illite or mixtures thereof. In certain embodiments, clay is selected from, by way of non-limiting example, laponite, bentonite, hectorite, saponite, montmorillonites or mixtures thereof.

In certain embodiments, the mucoadhesive agent is provided in an amount sufficient to provide exposure of the corticosteroid to a surface of the gastrointestinal tract (e.g., the surface of the esophagus) for a sufficient period of time such that the symptoms of and/or inflammation associated with inflammatory diseases involving the gastrointestinal tract (e.g., of the esophagus, stomach and/or digestive tract) are reduced following administration of the corticosteroid containing oral dosage form as single dose or multiple dose administration.

In some embodiments, the mucoadhesive agent is selected and selected in an amount sufficient to cause the corticosteroid containing pharmaceutical composition to adhere to or resides upon a surface of the gastrointestinal tract (e.g., the surface of the esophagus) for 5 seconds, 10 seconds, 15 seconds, 30 seconds, 45 seconds, or 1 minute following application to the surface of the gastrointestinal tract (e.g., the surface of the esophagus), such as by oral administration. In certain embodiments, the mucoadhesive agent is selected and selected in an amount sufficient to cause the corticosteroid containing composition to adhere to or reside upon the surface of the gastrointestinal tract (e.g., the surface of the esophagus) for 1.5, 2, 3, 4, 5, 6, 7, 8, 9, 10, 15, 20, 25, 30, 35, 40, 45, 50, 55 or 60 minutes after application to the surface of the gastrointestinal tract (e.g., the surface of the esophagus). In some embodiments, the amount of corticosteroid containing composition that adheres to a surface of the gastrointestinal tract (e.g., the surface of the esophagus) for 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes is at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90% or at least 95% by weight after administration to the surface of the gastrointestinal tract (e.g., the surface of the esophagus). In specific embodiments, at least 50% of the pharmaceutical composition adheres to or resides upon the surface of the gastrointestinal tract (e.g., the surface of the esophagus) for at least 1 or at least 15 minutes following application to the surface of the gastrointestinal tract (e.g., the surface of the esophagus).

In certain embodiments, the mucoadhesive agent is selected and selected in an amount sufficient to cause the corticosteroid to adhere to and/or be absorbed at a surface of the gastrointestinal tract (e.g., the surface of the esophagus) after 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes following application to the surface of the gastrointestinal tract (e.g., the surface of the esophagus), such as by oral administration. In some embodiments, the amount of corticosteroid that adheres to and/or is absorbed at the surface of the gastrointestinal tract (i.e. the sum of the amount that adheres to or resides upon the esophagus and the amount absorbed by the inflamed gastrointestinal) for 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes is at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90% or at least 95% by weight following administration to the surface of the gastrointestinal tract (e.g., the surface of the esophagus). In some embodiments, at least 50% of the corticosteroid adheres to and/or is absorbed by the ga surface of the gastrointestinal tract (e.g., the surface of the esophagus) at least 1 or at least 15 minutes after administration to the surface of the gastrointestinal tract (e.g., the surface of the esophagus).

In specific embodiments, following oral administration of a composition described herein to the esophagus (e.g., following initial swallowing or drinking of the composition), at least 1%, 2%, 3%, 4%, 5%, 6%, 7%, 8%, 9%, 10%, 15%, 20%, 30%, 40%, 50%, 60%, 70%, 80%, 90% or 95% by weight of the corticosteroid or composition administered is present within the esophagus (e.g., as measured by gamma scintigraphy) after at least 5 seconds, 10 seconds, 15 seconds, 20 seconds, 25 seconds, 30 seconds, 40 seconds, 45 seconds, 50 seconds, or 1, 1.5, 2, 3, 4, 5, 6, 7, 8, 9, 10, 15, 20, 25, 30, 35, 40, 45, 50, 55 or 60 minutes following application of the composition to the esophagus. In certain instances, even small differences (e.g., increases) in adherence times (e.g., residence times) between formulations can result in therapeutically significant or clinically significant results or improvements.

In some embodiments, the weight percent of corticosteroid containing composition that adheres to or resides upon the surface of the gastrointestinal tract (e.g., the surface of the esophagus) after 5, 10, 15, 30, or 45 seconds or 1, 1.5, 2, 3, 4, 5, 6, 7, 8, 9, 10, 15, 20, 25, 30, 35, 40, 45, 50, 55 or 60 minutes is greater than (e.g., more than 1.1×, 1.2×, 1.3×, 1.4×, 1.5×, 2×, 3×, 4×, 5×) the weight percent of a control composition that adheres the surface of the gastrointestinal tract (e.g., the surface of the esophagus). In certain embodiments, the control composition contains the same amount of corticosteroid, 4 mL of aqueous formulation and 10 packs of Splenda® (distributed by McNeil Nutritionals, LLC Fort Washington, Pa. 19034-2299) for every 0.5 mg, 1 mg, or 2 mg of corticosteroid (e.g., 2 Respules of Pulmicort®, each a 2 mL suspension containing 0.25 mg, 0.5 mg, or 1 mg of micronized budesonide). For example, in some embodiments for a budesonide containing pharmaceutical composition, the control composition contains 4 mL Pulmicort® and 10 packets of Splenda®. In some embodiments, the control composition contains the same amount of corticosteroid, 8 mL of aqueous formulation and 20 packs of Splenda® (packs of Splenda® comprise about 1 g and are distributed by McNeil Nutritionals, LLC Fort Washington, Pa. 19034-2299) for every 0.5 mg, 1 mg, or 2 mg of corticosteroid (e.g., 4 Respules of Pulmicort®, each a 2 mL suspension containing 0.25 mg, 0.5 mg, or 1 mg of micronized budesonide). In certain embodiments, the control composition comprises the same volume and the same corticosteroid in the same amount as present in the stable oral pharmaceutical composition, and has a viscosity of about 1 cP at 25° C. and a shear rate of about 13.2 sec$^{-1}$ (e.g., Respules of Pulmicort®). Formulations described herein as control compositions are also contemplated herein. The weight percent of corticosteroid containing composition that adheres to or resides upon the surface of the gastrointestinal tract (e.g., the surface of the esophagus) may be determined by dividing the amount of corticosteroid containing composition adhering to the surface of the gastrointestinal tract (e.g., the surface of the esophagus) by the total amount of corticosteroid containing composition that was administered to surface of the gastrointestinal tract (e.g., the surface of the esophagus) and multiplying the result by 100%. Likewise, the weight percent of control composition that adheres to a surface of the gastrointestinal tract (e.g., the surface of the esophagus) may be determined by dividing the amount of control composition adhering to a surface of the gastrointestinal tract (e.g., the surface of the esophagus) by the total amount of control composition that was administered to surface of the gastrointestinal tract (e.g., the surface of the esophagus) and multiplying the result by 100%. In some embodiments, the amount of corticosteroid that adheres to or is absorbed by surface of the gastrointestinal tract (e.g., the surface of the esophagus) after 5, 10, 15, 30, or 45 seconds or 1, 1.5, 2, 3, 4, 5, 6, 7, 8, 9, 10, 15, 20, 25, 30, 35, 40, 45, 50, 55 or 60 minutes is greater than (e.g., more than 1.1×, 1.2×, 1.3×, 1.4×, 1.5×, 2×, 3×, 4×, 5×) a control composition containing the same amount of corticosteroid, e.g., 4 mL of aqueous formulation and 10 packs of Splenda® for every 0.5 mg or 1 mg of corticosteroid. One pack of Splenda® contains about one gram of a mixture comprising dextrose, maltodextrin and sucralose.

In certain embodiments, a pharmaceutical composition described herein has a greater mucoadhesive characteristic and a decreased viscosity when compared to a control composition containing the same amount of corticosteroid. In some embodiments, a pharmaceutical composition described herein has a substantially similar mucoadhesive characteristic and a decreased viscosity when compared to a control composition. In certain embodiments, a pharmaceutical composition described herein adheres to or resides upon a gastrointestinal site (e.g., esophagus) for a length of time greater than or equal to that of a control composition while having a viscosity that is less than or equal to the control composition. In specific embodiments, when the pharmaceutical composition described herein adheres to or resides upon a gastrointestinal site (e.g., esophagus) for a length of time equal to that of a control composition, the viscosity of the pharmaceutical composition described herein is less than that of the control composition. In certain embodiments, the control composition used here contains 4 mL Pulmicort® (e.g., 0.25 mg or 0.5 mg budesonide per 2 mL dose) and 10 packets of Splenda® (e.g., 4 mL of aqueous formulation and 10 packs of Splenda® for every 0.5 mg or 1 mg of corticosteroid). In some embodiments, the control composition contains the same amount of corticosteroid, 8 mL of aqueous formulation and 20 packs of Splenda® (packs of Splenda® comprise about 1 g and are distributed by McNeil Nutritionals, LLC Fort Washington, Pa. 19034-2299) for every 0.5 mg, 1 mg, or 2 mg of corticosteroid (e.g., 4 Respules of Pulmicort®, each a 2 mL suspension containing 0.25 mg, 0.5 mg, or 1 mg of micronized budesonide).

In certain embodiments, adherence and/or absorption of a pharmaceutical composition or corticosteroid described herein to a surface of the gastrointestinal tract (e.g., the surface of the esophagus) may be determined by scintigraphy or by an assay. In some embodiments, such determinations are performed in vivo or in vitro. In certain embodiments, in vivo scintigraphy may include combining a pharmaceutical composition described herein with a detectable radioisotope, administering the labeled composition to a subject and detecting and/or measuring the adherence of the pharmaceutical composition or corticosteroid to the surface of the gastrointestinal tract (e.g., the surface of the esophagus) with a device (e.g., camera) that detects and/or measures radioactivity. In some embodiments, in vivo scintigraphy may include linking a corticosteroid described herein with a detectable radioisotope, formulating the labeled corticosteroid into a composition described herein, administering the composition to a subject and detecting and/or measuring the adherence of the pharmaceutical composition or corticosteroid to the surface of the gastrointestinal tract (e.g., the surface of the esophagus) with a device (e.g., camera) that detects and/or measures radioactivity. In certain embodiments, an in vitro assay for detecting adherence of a pharmaceutical composition or corticosteroid described herein to a surface of the gastrointestinal tract (e.g., the surface of the esophagus) may include applying a composition described herein to a distal portion of a strip of gastrointestinal surface tissue (e.g., porcine esophageal tissue) and subjecting the composition to a flow of artificial saliva in the direction of the opposite distal portion of the strip. Determination of adherence of the composition and/or corticosteroid may be determined at a given time by detecting either the amount of composition and/or corticosteroid eluted or the amount of composition and/or corticosteroid remaining on the gastrointestinal surface tissue.

In some embodiments, a pharmaceutical composition described herein (or a corticosteroid administered in a composition described herein) has an esophageal transit time of more than 5, 10, 15, 30 or 45 seconds or 1, 1.5, 2, 3, 4, 5, 6, 7, 8, 9, 10, 15, 20, 25, 30, 35, 40, 45, 50, 55 or 60 minutes, wherein the esophageal transit time is the lag time from administration (e.g., orally and/or to the esophagus) of a pharmaceutical composition described herein until activity falls to ≤10% of peak activity. In certain embodiments, a pharmaceutical composition described herein (or a corticosteroid administered in a composition described herein) has an esophageal mean transit time of about 5, 10, 15, 30 or 45 seconds or 1, 1.5, 2, 3, 4, 5, 6, 7, 8, 9, 10, 15, 20, 25, 30, 35, 40, 45, 50, 55 or 60 minutes. In some embodiments, a pharmaceutical composition described herein (or a corticosteroid administered in a composition described herein) has an esophageal emptying of less than 1%, 2%, 3%, 4%, 5%, 6%, 7%, 8%, 9%, 10%, 15%, 20%, 30%, 40%, 50%, 60%, 70%, 80%, 90%, 95%, 98%, or 99% ten seconds after peak activity.

Optional viscosity-enhancing excipients used in pharmaceutical compositions described herein include, by way of non-limiting example, a crosslinked poly(acrylic acid) (e.g., Carbopol 974P), glycerine, a carbomer homopolymer, a carbomer copolymer, acacia (gum arabic), agar, aluminum magnesium silicate, sodium alginate, sodium stearate, bladderwrack, bentonite, carbomer, carrageenan, Carbopol, cellulose, microcrystalline cellulose (MCC), ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500) gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, carboxymethyl-cellulose (CMC) (including, e.g., sodium carboxymethyl-cellulose (NaCMC)), silicon dioxide, polyvinylpyrrolidone (PVP: povidone), Splenda® (dextrose, maltodextrin and sucralose) or combinations thereof.

In certain embodiments, a pharmaceutical composition described herein is a non-newtonian fluid or a newtonian fluid. In some embodiments, a pharmaceutical composition described herein is a non-newtonian fluid. In specific embodiments, the non-newtonian fluid is a plastic, pseudo-plastic or dilatant non-newtonian fluid. In some specific embodiments, the non-newtonian fluid is thixotropic. In certain embodiments, the non-newtonian fluid composition thins with shear, and thickens upon the absence of shear. Thus, in some embodiments, provided herein is a fluid pharmaceutical composition that is suitable for easy pouring following mild or moderate agitation. Furthermore, in some embodiments, provided herein is a fluid pharmaceutical composition that while being suitable for easy pouring following mild or moderate agitation becomes viscous enough upon oral administration to allow the pharmaceutical composition to at least partially coat the esophagus and topically deliver a therapeutically effective amount of corticosteroid to the esophagus.

In certain embodiments, the pharmaceutical compositions provided herein are used to treat, prevent or alleviate inflammatory diseases involving the gastrointestinal tract, including the esophagus, stomach and/or digestive tract. In some embodiments, the pharmaceutical composition is in liquid form. Liquid forms include, by way of non-limiting example, emulsions, solutions, suspensions, syrups, slurries, dispersions, colloids and the like. Also provided are pharmaceutical compositions comprising a corticosteroid (e.g., a topical corticosteroid, such as, for example, budesonide) and a mucoadhesive agent in the form of a dissolving tablet, a dissolving wafer, a capsule, or a gel capsule. In some embodiments, a pharmaceutical composition described herein is in liquid, semi-solid or solid form. In specific embodiments, a pharmaceutical composition described herein is in semi-solid form, e.g., a gel, a gel matrix, a cream, a paste, or the like. In some embodiments, semi-solid forms comprise a liquid vehicle.

The methods and compositions of the present invention are used by individuals of any age. By "individual" is meant any animal, for example, a mammal, or, for example, a human, including, for example, patients in need of treatment.

By "individual" is meant any animal, for example, a mammal, or, for example, a human, including, for example, patients in need of treatment. In some embodiments, the human is a child. Children are often in need of treatment because they tend to have the most difficulty using the puff and swallow technique. In certain embodiments, the methods of the present invention are used for individuals of any age, including adults.

In certain embodiments, the compositions provided herein are prepared utilizing any suitable source of active agents. In some embodiments, corticosteroid (e.g., budesonide) used in the compositions described herein are neat corticosteroid (e.g., budesonide). In some embodiments, the neat corticosteroid (e.g., budesonide) is neat, bulk corticosteroid. In certain embodiments, the neat corticosteroid (e.g., budesonide) is powder corticosteroid (e.g., budesonide). In specific embodiments, the neat corticosteroid (e.g., budesonide) is micronized corticosteroid (e.g., budesonide).

In some embodiments, the corticosteroid is administered in a commercially available formulation. In other embodiments, the corticosteroid is administered in a composition comprising a commercially available formulation of a corticosteroid. For example, in some embodiments, the corticosteroid containing composition comprises a commercially available formulation and an excipient, such as an excipient that imparts a mucoadhesive characteristic to the composition and/or a diluent. In some embodiments, wherein the corticosteroid is budesonide, the commercially available formulation is Pulmicort Respules®. In other embodiments, wherein the corticosteroid is budesonide, the commercially available formulation is Rhinocort Aqua®. In some embodiments, wherein the corticosteroid is fluticasone, the commercially available formulation is Flonase®. In some embodiments, the ratio of commercially available formulation to the optional diluent is between about 1:0.5 and about 1:100. Diluents include any pharmaceutically acceptable oral diluent including, e.g., powder diluents (such as talc) and liquid diluents (such as water, ethanol and combinations thereof). In certain embodiments, the commercially available formulation is Entocort®. In certain embodiments, Entocort® formulations are dissolved and/or dispersed in an aqueous vehicle. In specific embodiments, the Entocort® formulation is dispersed in a liquid vehicle that has a pH sufficient to remove the enteric coating from the budesonide particles. In other embodiments, the Entocort® formulation is pre-treated with a solvent having a pH sufficient to remove the enteric coating from the budesonide particles therein, and the particles are subsequently formulated into a composition described herein.

In certain embodiments, the corticosteroid containing composition comprises micronized budesonide, disodium edetate, sodium chloride, sodium citrate, citric acid, polysorbate (e.g., polysorbate 80), water, and optionally one or more excipients, wherein the excipients are selected from any of those recited herein. In certain embodiments, the composition comprises about 0.1 mg to about 1.0 mg budesonide/2 mL (or about 0.05 mg to about 0.5 mg per gram) of composition. In some embodiments, the composition comprises about 0.2 mg to about 0.6 mg budesonide/2 mL (or about 0.1 mg to about 0.3 mg per gram) of composition. In specific embodiments, the composition comprises about 0.25 mg/2 mL composition. In other specific embodiments, the composition comprises about 0.5 mg/2 mL composition.

In other embodiments, the corticosteroid containing composition comprises micronized budesonide, microcrystalline cellulose (MCC), carboxymethyl cellulose (including, e.g., carboxymethyl cellulose sodium), dextrose, polysorbate (e.g., polysorbate 80), disodium edetate, potassium sorbate, water, optionally hydrochloric acid and optionally one or more excipients, wherein the excipients are selected from any of those recited herein. In specific embodiments, the composition has a pH of about 4.5. In some embodiments, the composition comprises about 0.1 mg to about 1.0 mg of budesonide/g of composition. In certain embodiments, the composition comprises about 0.3 mg to about 0.6 mg of budesonide/g of composition. In specific embodiments, the composition comprises about 0.4 mg or 0.44 mg of budesonide/g of composition. In certain specific embodiments, the composition comprises about 3.8 mg/8.6 g composition. In some embodiments, the composition comprises about 0.1 mg to about 1.0 mg of budesonide/mL of composition (about 0.01 to about 0.1% w/w). In certain embodiments, the composition comprises about 0.3 mg to about 0.8 mg of budesonide/nm of composition (about 0.03 to about 0.08% w/w). In specific embodiments, the composition comprises about 0.6 to about 0.7 mg of budesonide/mL of composition (about 0.06 to about 0.07% w/w). In more specific embodiments, the composition comprises about 0.63 mg of budesonide/mL of composition (about 0.063% w/w).

In some embodiments, the corticosteroid containing composition comprises microfine fluticasone propionate, microcrystalline cellulose, carboxymethyl cellulose (including, e.g., carboxymethyl cellulose sodium), dextrose, benzalkonium chloride, polysorbate (e.g., polysorbate 80), phenylethylalcohol, and optionally one or more excipients, wherein the excipients are selected from those recited herein. In some embodiments, the composition has a pH of between about 5 and about 7. In certain embodiments, the composition comprises about 20 to about 80 µg fluticasone propionate/mg composition. In some embodiments, the composition comprises about 40 to about 60 µg fluticasone propionate/mg composition. In specific embodiments, the composition comprises about 50 µg fluticasone propionate/mg composition. In some embodiments, the composition comprises about 0.02% w/w benzalkonium sodium and about 0.25% w/w phenylethyl alcohol.

Formulations

While the compositions of the present invention will typically be used in therapy for human patients, in certain embodiments, they are used in veterinary medicine to treat similar or identical diseases. In some embodiments, the compositions are used, for example, to treat mammals, including, but not limited to, primates and domesticated mammals. In some embodiments, the compositions are used, for example, to treat herbivores. The compositions of the present invention include geometric and optical isomers.

Pharmaceutical compositions suitable for use in the present invention include compositions wherein the active ingredient or ingredients are contained in an effective amount to achieve its intended purpose.

The exact dosage will depend upon the route of administration, the form in which the composition is adminstered, the subject to be treated, the age, body weight/height of the subject to be treated, and the preference and experience of the attending physician. In certain embodiments, the optimal concentration of the corticosteroid in the composition depends upon the specific corticosteroid used, the characteristics of the patient, and the nature of the inflammation for which the treatment is sought. In various embodiments, these factors are determined by those of skill in the medical and pharmaceutical arts in view of the present disclosure.

Generally, a therapeutically effective dose is desired. A therapeutically effective dose refers to the amount of the corticosteroid that results in a degree of amelioration of symptoms and/or inflammation relative to the status of such symptoms and/or inflammation prior to treatment. The dosage forms and methods of applying dosage forms containing effective amounts are within the scope of the instant invention. In various embodiments, the amount of corticosteroid (e.g., budesonide or fluticasone propionate) used in a method or in a composition described herein is from about 2.5 to 400 µg/kg of body weight per day, or for example, in the range of 5 to 300 µg/kg per day, or for example in the range of 5 to 200 µg/kg per day, or for example in the range of 5 to 100 µg/kg per day, or for example in the range of 10 to 100 µg/kg per day, or for example in the range of 10-50 µg/kg per day, or for example in the range of 10-100 µg/kg/day, or for example in the range of 5-50 µg/kg/day, or in an illustrative embodiment in the range of 10-60 µg/kg/day. In some embodiments, the amount of corticosteroid (e.g., budesonide or fluticasone propionate) used in a method, in a combination or a dose of a combination disclosed herein includes, by way of non-limiting example, about 50 µg to about 500 mg, about 50 µg to about 200 mg, about 50 µg to about 100 mg, about 50 µg to about 50 mg, about 100 µg to about 20 mg, about 250 µg to about 20 mg, about 250 µg to about 15 mg, about 250 µg to about 10 mg, about 250 µg to about 5 mg, about 300 µg to about 4 mg, about 350 µg to about 2 mg about 250 µg to about 3 mg, or about 500 µg to about 3 mg, about 375 µg to about 1.5 mg, or about 500 µg to about 2 mg, or about 1 mg to about 3 mg. In an illustrative embodiment, the dosage is provided in a sufficient volume to allow the composition to reach the esophagus in an effective amount. In some embodiments, a composition described herein comprises 1 or more doses. In certain embodiments, a composition described herein is contained in a multiple unit container. Thus, provided herein is a kit comprising a composition described herein and a container (e.g., a multiple unit or single unit container). In certain embodiments, provided herein is a composition or a kit comprising a composition that comprises from about 2 and about 180, about 10 to about 60, about 14 or about 30 doses.

In an illustrative embodiment a dosage or amount (including a divided dose) of corticosteroid is provided in a composition of sufficient volume to allow any of the compositions disclosed herein to reach the targeted and/or inflamed portion of the gastrointestinal tract, including, e.g., the esophagus, in an effective amount. In some embodiments, the effective amount of the composition delivered to the esophagus is an amount sufficient to coat or at least partially coat the esophagus, and deliver the composition to the affected areas, including by way of example only, the lower esophagus, the esophageal-stomach juncture, the stomach and/or the duodenum. In certain embodiments, a composition described herein has a volume of, for example about 1-50 mL, or for example about 1-40 mL, or for example about 1-30 mL, or for example about 1-25 mL, or for example about 1-20 mL, or for example about 5-25 mL, or for example about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example, about 5 mL, or for example about 6-14 mL, or for example about 8-12 n×L, or for example, about 9-11 mL, or for example, about 10 mL. In more specific embodiments, about 0.25 mg to about 6 mg, about 0.375 mg, about 0.5 mg, about 0.75 mg, about 1 mg, about 1.25 mg, about 1.5 mg, or about 2 mg of corticosteroid (e.g., budesonide) is formulated into a single or unit dose of a pharmaceutical composition described herein, the single or unit dose having a total volume of about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example, about 5 mL, or for example, about 6-14 mL, or for example about 8-12 mL, or for example, about 9-11 mL, or for example, about 10 mL. As discussed herein, "liquid" encompasses slurries, solutions, suspensions, dispersions or any combination thereof, depending on the solubilities and amounts of the individual components and the vehicles and solvents used. In some embodiments, an appropriate palatable dosage is in a volume sufficient to coat or at least partially coat the esophagus, and in an illustrative embodiment, the volume is sufficient to coat or at least partially coat the esophagus and deliver the corticosteroid to the affected areas, including by way of example only, the lower esophagus, the esophageal-stomach juncture, the stomach and/or the duodenum. The composition may be delivered, for example, four times a day, three times a day, twice a day, once a day, every other day, three times a week, twice a week, or once a week. The dosage may, for example, be divided into multiple doses throughout the day, or be provided, for example, in four, three, two, or one dose a day. In certain instances, administration more frequent administration (e.g., b.i.d. versus once a day) provides for a shorter overall therapy or a quicker onset of symptom resolution. In one illustrative example, the dose is provided once a day.

In certain embodiments, a dose or composition described herein is administered with food. In some embodiments, a dose or composition described herein is administered without food. In certain embodiments, a dose or composition described herein is administered in a fed or fasted state. In some embodiments, a dose or composition described herein is administered in the morning, in the afternoon, in the evening, at night, or a combination thereof. In some embodiments, the dose is administered at night. In another aspect, the dose is administered about 30 minutes prior to bed, with no food or water given after administration of the compositions herein. In yet another embodiment of the instant invention, the dose is administered prior to bedtime, wherein after administration of the composition, the patient or individual is in a substantially supine position for at least 30 minutes, at least 1 hour, at least 2 hours, at least 4 hours or at least 8 hours.

In some embodiments, provided herein are methods of treating, preventing, or alleviating inflammation or symptoms associated with inflammation of the gastrointestinal tract, e.g., the esophagus, comprising administering to an individual in need thereof a single unit dose of a pharmaceutical composition described herein from a multidose container. In specific embodiments, administering a single unit dose from a multi dose container comprises (1) shaking a multidose container, the multidose container comprising at least one unit dose of a pharmaceutical composition described herein; (2) pouring (or otherwise dispensing) a single unit dose from the multidose container into an administration device (e.g., a device suitable for administering to a human individual, such as a spoon, cup or syringe); and (3) administering the single unit dose to the individual in need thereof. In more specific embodiments, shaking of the multidose container occurs until the fluid therein has a viscosity suitable for pouring (e.g., easy pouring). In some specific embodiments, the process further comprises waiting after pouring the single unit dose and prior to administering the single unit dose to the individual in need thereof. In specific embodiments, the wait time is a time sufficient to allow the viscosity of composition to achieve a desired level, e.g., a viscosity to improve the coating capabilities of the composition. In some embodiments, the wait time is, e.g., about 3 seconds, or more; about 5 seconds, or more; about 10 seconds, or more; about 15 seconds, or more; about 20 seconds, or more; about 25 seconds, or more; about 30 seconds, or more; about 40 seconds, or more; about 45 seconds, or more; about 50 seconds, or more; or about 60 seconds, or more. In other specific embodiments, the composition is administered immediately following pouring the composition into the administration device. In some embodiments, the process comprises shaking the multidose container well.

In some embodiments, initial treatment continues, for example, for about 3 days to 2 weeks for an acute condition, or about 4 weeks to about 16 weeks for a chronic condition, or about 8 weeks to about 12 weeks for a chronic condition. In various embodiments, longer therapy is needed, such as, for example, therapy similar to chronic therapy for persistent asthma. In some aspects of the present invention, patients are, for example, be treated for up to 6 months, or up to one year. In certain aspects, maintenance treatments last up to or longer than one year. In some embodiments, patients are treated on a maintenance basis or on an as needed basis during a problematic episode, depending on the severity of the condition. In certain embodiments, patients are treated on a rotating treatment basis, where treatment is provided for a period of time and then the patient is taken off of the drug for a period before treatment resumes again. When off the drug, the patient may be given no treatment, treatment with another medication, or treatment with a reduced dosage. In certain embodiments, patients are given treatment with a higher dose of the composition until a desired reduced disease state is achieved, and then continued on a lower dose of the composition.

In some embodiments, the corticosteroid is present in a pharmaceutical composition described herein in any effective amount. In some embodiments, an effective amount is an amount sufficient to reduce inflammation or symptoms of inflammation associated with an inflammatory disease or condition of the gastrointestinal tract (e.g., the esophagus) as compared to the level of inflammation or symptoms of inflammation associated with an inflammatory disease prior to administration of the effective amount. In certain embodiments, effective amount is an amount sufficient to maintain a reduction in inflammation or symptoms of inflammation achieved in any manner including, but not limited to, by the administration of an effective amount sufficient to achieve such a reduction. In some embodiments, the effective amount is about 0.05 mg to about 10 mg, about 0.05 mg to about 7.5 mg, about 0.05 mg to about 5 mg, about 0.25 mg to about 3 mg, about 0.25 mg to about 2.5 mg, about 0.5 mg to about 3 mg, about 0.5 mg to about 2 mg, about 0.5 mg to about 0.1 mg, about 0.5 mg to about 5 mg, about 0.5 mg to about 4 mg, about 1 mg to about 4 mg, about 1 mg to about 3 mg, about 2 mg to about 3 mg, or about 2 mg to about 4 mg. In specific embodiments, the effective amount of corticosteroid is about 0.05 mg, about 0.1 mg, about 0.15 mg, about 0.25 mg, about 0.3 mg, about 0.35 mg, about 0.4 mg, about 0.37 mg, about 0.375 mg, about 0.7 mg, about 0.8 mg, about 0.75 mg, about 1 mg, about 1.2 mg, about 1.25 mg, about 1.3 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, or about 7.5 mg or more. In certain embodiments, the corticosteroid is present in a pharmaceutical composition at a concentration of about 0.01 mg/mL to about 2 mg/mL of composition. In specific embodiments, the corticosteroid is present in a pharmaceutical composition at a concentration of about 0.01 mg/mL to about 1.5 mg/mL, about 0.03 mg/mL to about 1.5 mg/mL, about 0.05 mg/mL to about 1.5 mg/mL, or about 0.07 mg/mL to about 1.5 mg/mL. In more specific embodiments, the corticosteroid is present in a pharmaceutical composition at a concentration of about 0.07 mg/mL to about 1 mg/mL.

In specific embodiments, the composition described herein is an composition comprising a corticosteroid, dextrose, maltodextrin, edetate, citrate, polysorbate 80, an optional preservative, an optional flavoring agent, an optional sweetener, at least one additional excipient, and a liquid vehicle. In specific embodiments, the composition comprises a preservative. In further or alternative embodiments, the composition comprises a flavoring agent. In further or alternative embodiments, the liquid vehicle is an aqueous medium (e.g., water). In specific embodiments, corticosteroid particles (e.g., microparticles) are suspended in the aqueous medium.

In some embodiments, the corticosteroid is selected from, by way of non-limiting example, budesonide, fluticasone propionate and combinations thereof. In specific embodiments, corticosteroid (e.g., budesonide or fluticasone propionate) is present in a composition or formulation described herein in an amount of about 0.005 mg/mL to about 1.5 mg/mL, or about 0.01 mg/mL to about 1 mg/mL, about 0.01 mg/mL to about 5 mg/mL, about 0.01 mg/mL to about 3 mg/mL, about 0.01 mg/mL to about 2 mg/mL, about 0.01 mg/mL to about 1.5 mg/mL, about 0.05 mg/mL to about 0.5 mg/mL, about 0.05 mg/mL to about 0.4 mg/mL, about 0.07 mg/mL to about 1.5 mg/mL, or about 0.07 mg/mL to about 1 mg/mL. In more specific embodiments, budesonide is present in an amount of about 0.01 mg/mL to about 3 mg/mL, about 0.01 mg/mL to about 1.5 mg/mL, about 0.05 mg/mL to about 0.5 mg/mL, about 0.05 mg/mL to about 0.4 mg/mL, or about 0.07 mg/mL to about 1 mg/mL. In other specific embodiments, fluticasone propionate is present in an amount of about 0.005 mg/mL to about 1.5 mg/mL, or about 0.01 mg/mL to about 1 mg/mL.

In some embodiments, the volume of a composition or dose of a composition described herein is an amount sufficient to substantially coat (e.g., at least 50%, at least 60%, at least 70%, at least 80%, at least 90%, at least 95%, at least 98% or at least 99% of) the length of the esophagus of an individual to whom the composition is administered. In certain embodiments, the volume of a composition or a dose of a composition described herein is about 0.05 mL/cm esophageal length to about 1 mL/cm esophageal length, about 0.1 mL/cm esophageal length to about 0.8 mL/cm esophageal length, about 0.2 mL/cm esophageal length to about 0.6 mL/cm esophageal length, or about 0.3 nm/cm esophageal length to about 0.5 mL/cm esophageal length, wherein the esophageal length is the esophageal length of the individual to whom the composition is administered. In some embodiments, the volume of a composition or dose of a composition described herein is based on the esophageal length of an individual (e.g., male, female, or both) that is in the 50$^{th}$ percentile of height for their age. Therefore, in some embodiments, the volume of a composition or dose of a composition described herein is about 0.05 mL/cm esophageal length to about 1 mL/cm esophageal length, about 0.1 mL/cm esophageal length to about 0.8 mL/cm esophageal length, about 0.2 mL/cm esophageal length to about 0.6 mL/cm esophageal length, about 0.3 mL/cm esophageal length to about 0.5 mL/cm esophageal length, about 0.32 mL/cm esophageal length to about 0.41 mL/cm esophageal length, or about 0.3 mL/cm esophageal length to about 0.46 mL/cm esophageal length, wherein the esophageal length is the esophageal length of an individual having a height in the 50$^{th}$ percentile for the age of the individual to whom the composition is administered. In certain instances, esophageal length is the actual esophageal length of the individual or is calculated based on the equation: esophageal length=1.048 (cm)+ (0.167*height (cm)). In certain instances, for example, the 50$^{th}$ percentile height (CDC 2000) for male children age 2 is 87 cm, age 3 is 95 cm, age 4 is 102 cmn, age 5 is 109 cm, age 6 is 115 cm, age 7 is 122 cm, age 8 is 128 cm, age 9 is 134 cm, age 10 is 139 cm, age 11 is 144 cm, age 12 is 149 cm, age 13 is 156 cm age 14 is 164 cm, age 15 is 170 cm, age 16 is 174 cm, age 17 is 175 cm, and age 18 is 176 cm.

Furthermore, in certain embodiments, the amount of a therapeutic agent (e.g., a corticosteroid such as budesonide) in a composition or a dose of a composition described herein is about 0.005 mg/cm esophageal length to about 0.3 mg/cm esophageal length, about 0.008 mg/cm esophageal length to about 0.2 mg/cm esophageal length, about 0.01 mg/cm esophageal length to about 0.15 mg/cm esophageal length, or about 0.015 mg/cm esophageal length to about 0.1 mg/cm esophageal length, wherein the esophageal length is the esophageal length of the individual to whom the composition is administered. In some embodiments, the volume of a composition or dose of a composition described herein is based on the esophageal length of an individual (e.g., male, female, or both) that is in the 50$^{th}$ percentile of height for their age. Therefore, in some embodiments, the amount of a therapeutic agent (e.g., a corticosteroid such as budesonide) in a composition or dose of a composition described herein is about 0.005 mg/cm esophageal length to about 0.3 mg/cm esophageal length, about 0.008 mg/cm esophageal length to about 0.2 mg/cm esophageal length, about 0.01 mg/cm esophageal length to about 0.15 mg/cm esophageal length, or about 0.015 mg/cm esophageal length to about 0.1 mg/cm esophageal length, wherein the esophageal length is the esophageal length of an individual having a height in the 50$^{th}$ percentile for the age of the individual to whom the composition is administered.

In some embodiments, any pharmaceutical composition or dose of a pharmaceutical composition described herein is provided or administered in a volume sufficient to provide a bolus when orally administered to an individual. In certain embodiments, the composition has a volume that does not systemically deliver excessive amounts of the active agent. In some embodiments, the pharmaceutical composition or dose is provided in a volume sufficient to provide a bolus when administered to an individual, wherein the size of the bolus at the distal end of the esophagus (e.g., the size of the bolus prior, e.g., immediately prior, to entering or passing the lower esophageal sphincter) is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10% or less than 5% of size of the bolus that entered the esophagus (e.g., the size of the bolus after, e.g., immediately after, passing the upper esophageal sphincter). In some embodiments, the size of the bolus is determined as a measure of diameter or of volume. In certain embodiments, diameter of the sphincter can be determined using gamma scintigraphy techniques. In specific embodiments, the volume of the composition or dose is adjusted given the length and/or diameter of the esophagus of the individual to whom the composition or dose is administered.

In other illustrative embodiments of the invention, the compositions disclosed herein are provided in the form of a lozenge which may be dissolved in the mouth, thus reaching and at least partially coating the esophagus, and deliver the composition to the affected areas, including by way of example only, the lower esophagus, the esophageal-stomach juncture, the stomach and/or the duodenum. The lozenge or other similar dosage form (e.g., a tablet, capsule, or other solid), would dissolve in the mouth or esophagus to produce a solution that can then at least partially coat the esophagus, and thereafter deliver the composition to the affected areas, including by way of example only, the lower esophagus, the esophageal-stomach juncture, the stomach and/or the duodenum. Or, for children, infants or other patients that may have difficulty with a dissolving lozenge, the lozenge may be ground or otherwise dissolved in a small volume of water or other pharmaceutically suitable liquid, for example, reaching a total volume presented in embodiments herein. In other illustrative embodiments of the invention, the compositions disclosed herein are provided in the form of a tablet, a capsule, or, for example a gel capsule, designed for slow release and delivery to the gastrointestinal tract, including the esophagus.

In some embodiments, initial treatment continues, for example, for about 3 days to 2 weeks for an acute condition, or about 4 weeks to about 16 weeks for a chronic condition, or about 8 weeks to about 12 weeks for a chronic condition. In various embodiments, longer therapy is needed, such as, for example, therapy similar to chronic therapy for persistent asthma. In some aspects of the present invention, patients are, for example, be treated for up to 6 months, or up to one year. In certain aspects, maintenance treatment last up to or longer than one year. In some embodiments, patients are treated on a maintenance basis or on an as needed basis during a problematic episode, depending on the severity of the condition. In certain embodiments, patients are treated on a rotating treatment basis, where treatment is provided for a period of time and then the patient is taken off of the drug for a period before treatment resumes again. When off the drug, the patient may be given no treatment, treatment with another medication, dietary therapy, or treatment with a reduced dosage. In certain embodiments, patients are given treatment with a higher dose of the composition until a desired reduced disease state is achieved, and then continued on a lower dose of the composition. In certain embodiments, a patient combines treatment with a composition described herein with a treatment with another medication, and/or dietary therapy. In certain embodiments, patients are given treatment with a higher dose of the composition until a desired reduced disease state is achieved, and then continued on a lower dose of the composition.

In some embodiments, methods of treatment described herein include intermittent or continuous treatments. In certain embodiments, a method of treating gastrointestinal inflammation described herein includes prophylactic treatment of gastrointestinal inflammation (e.g., a treatment that prevents symptoms and/or inflammation from occurring). In some embodiments, a method of treating gastrointestinal inflammation described herein includes a method of prolonging and/or maintaining remission of gastrointestinal inflammation by administering or continuing to administer a pharmaceutical composition as described herein after inflammation and/or symptoms of inflammation are in remission. In specific embodiments, prophylactic and/or remissive therapies optionally comprise administration of a composition described herein comprising a reduced amount of corticosteroid compared to the amount of corticosteroid utilized when the inflammation and/or symptoms of inflammation are not in remission.

In some embodiments, provided herein is a method of diagnosing an individual with gastrointestinal inflammation (e.g., EoE) by administering a pharmaceutical composition described herein; and determining the efficacy of such a treatment. In certain instances, the individual is a patient who has gastrointestinal inflammation and/or symptoms thereof that are refractory to at least one acid inhibitor (e.g., PPI and/or H2A). In some embodiments, effective treatment of the gastrointestinal inflammation with a composition described herein is a positive indication of EoE. In certain embodiments, this method of diagnosis is used instead of an esophageal biopsy.

In various embodiments, the compositions of the present invention include pharmaceutically acceptable salts. Pharmaceutically acceptable salts are generally well known to those of ordinary skill in the art and include, by way of non-limiting example, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20.sup.th ed.) Lippincott, Williams & Wilkins (2000). In specific embodiments, pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate. In certain embodiments, such salts are used for any of the corticosteroids described herein.

Depending on the specific conditions being treated, the compositions may be formulated into liquid or solid dosage forms and administered systemically or locally. In some embodiments, the agents are delivered, for example, in a timed- or sustained-low release form as is known to those skilled in the art. Techniques for formulation and administration may be found in Remnington: The Science and Practice of Pharmacy (20th ed.) Lippincott, Williams & Wilkins (2000).

In addition to the active or actives, various embodiments of the present invention provide for pharmaceutical compositions that contain suitable pharmaceutically acceptable excipients and auxiliaries. For example, in some embodiments, pharmaceutically acceptable excipients and/or auxiliaries are used to formulate the corticosteroids herein disclosed for the practice of the invention into dosages suitable for systemic administration is within the scope of the invention. In some embodiments, the corticosteroid is formulated readily using pharmaceutically acceptable excipients and/or auxiliaries well known in the art into dosages suitable for oral administration. Such excipients and/or auxiliaries enable the compositions of the invention to be formulated as tablets, pills, dragees, capsules, liquids, soft chews, creams, pastes, chewable tablets, gels or gel matrices, syrups, slurries, suspensions, gums, lozenges, and the like, for oral ingestion by a patient to be treated. In certain instances, oral formulations (e.g., suspensions, creams or gel matrices) are formulated such that upon oral administration, an interface layer between the oral formulation (e.g., suspension, cream or gel matrix) and a surface of the gastrointestinal tract (e.g., the surface of the esophagus) is formed. In some instances, an oral formulation (e.g., suspensions, creams or gel matrices) in contact with a surface of the gastrointestinal tract (e.g., the surface of the esophagus) delivers a corticosteroid onto and/or through the surface of the gastrointestinal tract (e.g., the surface of the esophagus) via the interface layer and as the oral formulations (e.g., suspensions, creams or gel matrices) near the interface layer is depleted of corticosteroid, a concentration gradient results. In certain instances, portions of the oral formulations (e.g., suspensions, creams or gel matrices) with high concentrations of corticosteroid relative to the portions of the oral formulations (e.g., suspensions, creams or gel matrices) proximate to the interface layer replenishes corticosteroid in the portion of the oral formulations (e.g., suspensions, creams or gel matrices) proximate to the interface layer. In certain instances, upon oral administration of an oral formulation described herein to an individual, an interface layer is formed between a surface of the gastrointestinal tract (e.g., the surface of the esophagus) and a mixture of the oral formulation (e.g., chewable tablet) and saliva of the individual.

In certain embodiments, pharmaceutical preparations for oral use are obtained by combining the corticosteroids with solid excipients, optionally grinding a resulting mixture, and processing the mixture of granules, after adding suitable auxiliaries, if desired, to obtain tablets or dragee cores. Suitable excipients include, by way of non-limiting example, fillers such as sugars or starches, including dextrose, lactose, maltodextrin, sucrose, sucralose, mannitol, or sorbitol; cellulose preparations, for example, maize starch, wheat starch, rice starch, potato starch, or a combination thereof. Disintegrating agents are optionally added, such as the cross-linked polyvinylpyrrolidone, agar, or alginic acid or a salt thereof such as sodium alginate. In some embodiments, the pharmaceutical compositions used herein include excipients suitable for rendering the dissolving tablet palatable, such as sweeteners or flavoring agents.

In some embodiments, the pharmaceutical compositions described herein are in liquid form. Appropriate excipients for use in liquid form pharmaceutical compositions include, for example, those that increase the mucoadhesive character of the liquid composition. Optional excipients also include, by way of non-limiting example, those that render the liquid composition palatable or increase the viscosity of the liquid composition. Optional excipients that increase palatability include, by way of non-limiting example, sugars, including dextrose, lactose, sucrose, sucralose, maltodextrin, mannitol, or sorbitol; honey, combinations thereof, or the like.

Any of the compositions or formulations described herein optionally comprise one or more viscosity enhancing agent, optionally comprise one or more binder, optionally comprise one or more filler, optionally comprise one or more lubricant, optionally comprise one or more solvent, optionally comprise one or more suspension agent, optionally comprise one or more flavoring agent, optionally comprise one or more coloring agent, optionally comprise one or more sweetener, optionally comprise one or more preservative, optionally comprise one or more antioxidant, optionally comprise one or more buffering agent, optionally comprise one or more humectant, optionally comprise one or more chelating agent, optionally comprise one or more surfactant, or combinations thereof.

Preservatives include, by way of non-limiting example, benzalkonium chloride, cetrimide (cetyltrimethylammonium bromide), benzoic acid, benzyl alcohol, methyl-, ethyl-, propyl- and butyl-esters of para-hydroxybenzoic acid, chlorhexidine, chlorobutanol, phenylmercuric acetate, borate and nitrate, potassium sorbate, sodium benzoate, sorbic acid, thiomersal (mercurithiosalicylate), combinations thereof, or the like. Compositions and formulations described herein optionally include about 0.1% w/w to about 5% w/w, about 0.1% w/w to about 3% w/w, about 0.1% w/w to about 1% w/w, about 0.1% w/w to about 0.5% w/w, about 0.2% w/w of one or more preservative(s).

Antioxidants include, by way of non-limiting example, ascorbyl palmitate, butylated hydroxyanisole, butylated hydroxytoluene, monothioglycerol, sodium ascorbate, sodium formaldehyde sulfoxylate, sodium metabisulfite, BHT, BHA, sodium bisulfite, vitamin E or a derivative thereof, propyl gallate, edetate (EDTA) (e.g., disodium edetate), Diethylenetriaminepentaacetic acid (DTPA), Triglycollamate (NT), combinations thereof, or the like. Compositions and formulations described herein optionally include of about 0.01% w/w to about 1% w/w, about 0.01% w/w to about 0.5% w/w, about 0.01% w/w to about 0.3% w/w, or about 0.01% w/w to about 0.1% w/w one or more antioxidants).

Buffering agents include, by way of non-limiting example, citrate buffers (i.e., citric acid and citrate), phosphate buffers, acetate buffers, combinations thereof, or the like.

As used herein, "citrate" includes all compounds of Formula I wherein each R is independently selected from an H and a negative charge (e.g., as a salt or as a disassociated salt or acid). In certain embodiments, citrate is selected from, by way of non-limiting example, sodium citrate, citric acid and the like.

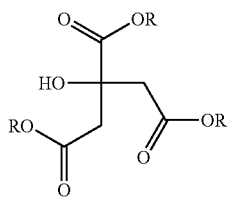

Formula I

Humectants include, by way of non-limiting example, glycerine, propylene glycol, ethylene glycol, glyceryl triacetate, polyols (e.g., sorbitol, xylitol, maltitol, polydextrose), and the like. Compositions and formulations described herein optionally include about 0.1% w/w to about 10% w/w, about 1% w/w to about 10% w/w, about 1% to about 8% w/w, or about 5% w/w of a humectant. In certain embodiments, humectants inhibit precipitation and/or crystallization of one or more component of a composition or formulation described herein (e.g., a sweetener, mucoadhesive agent or a viscosity enhancing agent).

Chelating agents include, by way of non-limiting example, edetate (EDTA) (e.g., disodium edetate), Diethylenetriaminepentaacetic acid (DTPA), Triglycollamate (NT), or the like. Compositions and formulations described herein optionally include about 0.01% w/w to about 0.5% w/w, about 0.01% w/w to about 0.3% w/w, or about 0.01% w/w to about 0.1% w/w, or about 0.05% w/w of one or more chelating agent.

As used herein, "edetate" includes all compounds of Formula II wherein each R is independently selected from an H and a negative charge (e.g., as a salt or as a disassociated salt or acid). In certain embodiments, edetate is selected from, by way of non-limiting example, disodium edetate, calcium edetate, ethylenediaminetetraacetic acid and the like.

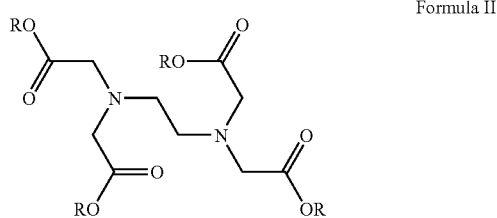

Formula II

In certain embodiments, sweeteners include, by way of non-limiting example, glycerin, acesulfame potassium (AceK), mono-ammonium glycyrrhizinate (e.g., Magnasweet®), sucrose, lactose, glucose, fructose, arabinose, xylose, ribose, mannose, galactose, dextrose, sorbose, sorbitol, mannitol, maltose, cellobiose, xylitol and the like. In some embodiments, flavoring agents include, by way of non-limiting example, peppermint, orange, bubble gum, wintergreen, grape and cherry.

Surfactants include, e.g., anionic, cationic, non-ionic, or zwitterionic surfactants, such as, by way of non-limiting example, polysorbate (e.g., polysorbate 20, polysorbate 60, polysorbate 40, polysorbate 80, polysorbate 81, polysorbate 85, polysorbate 120), bile acids or their salts (e.g., sodium taurocholates, sodium deoxytaurocholates, chenodeoxycholic acid, and ursodeoxycholic acid), nonoxynol or polyoxyethylene glycol fatty acid esters, pluronic or poloxamers such as Pluronic F68, Pluronic L44, Pluronic L101, combinations thereof, or the like. Compositions and formulations described herein optionally include about 0.001% w/w to about 0.5% w/w, about 0.001% w/w to about 0.3% w/w, or about 0.001% w/w to about 0.1% w/w of one or more surfactant.

Dragee cores are provided with suitable coatings. In some embodiments, concentrated sugar solutions are used for this purpose, which optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments are optionally added to the tablets or dragee coatings for identification or to characterize different combinations of active corticosteroid doses.

In various embodiments, pharmaceutical preparations that are used orally include push-fit capsules made of gelatin, as well as soft, sealed capsules made of gelatin, and a plasticizer, such as glycerol or sorbitol. In some embodiments, the push-fit capsules contain the active ingredient or ingredients in admixture with a filler, binder, lubricant, stabilizer or a combination thereof. Fillers include, by way of non-limiting example, lactose. Binders include, by way of non-limiting example, starches. Lubricants include, by way of non-limiting example, talc and magnesium stearate. In soft capsules, the corticosteroids may be dissolved or suspended in suitable liquids, such as fatty oils, liquid paraffin, or liquid polyethylene glycols (PEGs). In addition, stabilizers are optionally added.

In one embodiment, the present invention provides for a corticosteroid that has a low bioavailability. Due to the low bioavailability, the corticosteroid is used in certain embodiments of the invention, the corticosteroid remains in the gastrointestinal tract, for example, in the esophagus. In some embodiments, the low bioavailability results in decreased systemic side effects and complications, allowing patients with chronic conditions to receive treatment for longer periods of time.

In some embodiments, a pharmaceutical composition or dosage form described herein is a suspension or a solution comprising a corticosteroid (e.g., budesonide). In some embodiments, compositions (e.g., suspensions or solutions) comprise a certain concentration of corticosteroid (e.g., budesonide) that is dissolved in the liquid medium (e.g., the solvent or liquid vehicle used, such as water, alcohol, aqueous alcohol, or the like). In certain embodiments, the amount of corticosteroid (e.g., budesonide) dissolved in the liquid medium (e.g., in an equilibrated sample) is greater than 4 µg/mL, greater than 5 µg/mL, greater than 10 µg/mL, greater than 15 µg/mL, greater than 20 µg/mL, greater than 21 µg/mL, greater than 22 µg/mL, greater than 23 µg/mL, greater than 24 µg/mL, greater than 25 µg/mL, about 25 µg/mL, greater than 30 µg/mL, about 25 µg/mL to about 80 µg/mL, about 30 µg/mL to about 80 µg/mL, about 30 µg/mL, about 35 µg/mL, about 40 µg/mL, about 45 µg/mL, about 50 µg/mL, about 55 µg/mL, about 60 µg/mL, about 65 µg/mL, or about 70 µg/mL.

In some embodiments, compositions described herein comprise a certain concentration of budesonide that is dissolved in the liquid medium (e.g., the solvent or liquid vehicle used, such as water, alcohol, aqueous alcohol, or the like). In specific embodiments, the amount of R epimer of the dissolved budesonide (compared to the overall weight of the budesonide) is greater than 28% w/w, greater than 30% w/w, greater than 39% w/w, greater than 40%, about 39-50%, about 40-50%, less than 38% w/w, about 29%-37% w/w, less than 27% w/w, or the like. In some instances, the % epimers are obtained in a composition having an overall % R epimer (compared to overall budesonide) of about 50-55% w/w, or about 53-54% w/w. In certain instances, equilibration of the sample is accomplished once the concentration of the corticosteroid (e.g., budesonide) dissolved in the liquid is substantially stable, e.g., after 2 days, 3 days, 4 days, 5 days, a week, a month, or the like. In specific instances, equilibration of the sample is accomplished after 2 days.

In some embodiments, the corticosteroid is administered in a commercially available formulation. In other embodiments, the corticosteroid is administered in a composition comprising a commercially available formulation of a corticosteroid and formulated as described herein. For example, in some embodiments, the corticosteroid containing composition provided herein comprises a commercially available formulation and an excipient, such as a diluents, a flavoring agent, a mucoadhesive agent a viscosity enhancing agent, a binder, a filler, a lubricant, a solvent, a suspension agent, a coloring agent, a sweetener, a preservative, an antioxidant, a buffering agent, a humectant, a chelating agent, a surfactant, combinations thereof, or the like. In some embodiments, wherein the corticosteroid is budesonide, the commercially available formulation is Pulmicort Respules® (distributed by AstraZeneca, e.g., as set forth in NDA 20-929, which is hereby incorporated by reference in its entirety). In other embodiments, wherein the corticosteroid is budesonide, the commercially available formulation is Rhinocort Aqua® (distributed by AstraZeneca LP, Wilmington, Del. 19850, e.g., as set forth in NDA 20-746, which is, including all supplements, hereby incorporated herein by reference in its entirety). In still other embodiments, wherein the corticosteroid is budesonide, the commercially available formulation is Symbicort® (manufactured by AstraZeneca Dunkerque Production, Dunkerque, France, e.g., as set forth in NDA 21-929, which is, including all supplements, hereby incorporated herein by reference in its entirety). In some embodiments, wherein the corticosteroid is fluticasone, the commercially available formulation is Flonase®. In some embodiments, the ratio of commercially available formulation to the optional diluent is between about 1:0.5 and about 1:100. Diluents include any pharmaceutically acceptable oral diluent including, e.g., powder diluents (such as talc) and liquid diluents (such as water, ethanol and combinations thereof). In certain embodiments, the commercially available formulation is Entocort® (manufactured by AstraZeneca AB, S-151 85 Sodertalje, Sweden, distributed by Prometheus Laboratories Inc, San Diego, Calif. 92121, as set forth in NDA 21-324, which is, including all supplements, hereby incorporated herein by reference in its entirety). In certain embodiments, Entocort® formulations are dissolved and/or dispersed in an aqueous vehicle. In specific embodiments, the Entocort® formulation is dispersed in a liquid vehicle that has a pH sufficient to remove the enteric coating from the budesonide particles. In other embodiments, the Entocort® formulation is pre-treated with a solvent having a pH sufficient to remove the enteric coating from the budesonide particles therein, and the particles are subsequently formulated into a composition described herein.

In certain embodiments, a corticosteroid composition described herein comprises a corticosteroid, a commercially available formulation, and, optionally, one or more additional excipient. In some embodiments, a corticosteroid composition described herein comprises a corticosteroid formulated in a manner similar to a commercial formulation (e.g., lacking one or more of the active ingredients of the formulation), and, optionally, one or more additional excipient. The one or more additional excipients can be utilized to achieve a formulation as described herein. In specific embodiments, the commercially available formulation is Ultra XCID (manufactured by Matrixx Initiatives, Inc., Phoenix, Ariz.).

In certain embodiments, a composition provided herein comprises or is prepared by combining the components set forth in any of Tables 1-12. In various embodiments, one or more of maltodextrin, dextrose, HEC, CMC, MCC, Carbomer and HPMC are utilized therein.

TABLE 1

| Budesonide Composition #1 | |
|---|---|
| Ingredient | Amount |
| Budesonide | 1 mg to 150 mg |
| CMC, MCC, Carbomer, HPMC and/or HEC | 0.5 g to 10 g |
| Dextrose | 0 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 2

Budesonide Composition #2

| Ingredient | Amount |
| --- | --- |
| Budesonide | 1 mg to 150 mg |
| CMC, MCC, Carbomer, HPMC and/or HEC | 0 g to 10 g |
| Dextrose | 1 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 3

Budesonide Composition #3

| Ingredient | Amount |
| --- | --- |
| CMC, MCC, Carbomer, HPMC and/or HEC | 0 g to 10 g |
| Dextrose | 0 g to 100 g |
| Maltodextrin | 1 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 4

Budesonide Composition #4

| Ingredient | Amount |
| --- | --- |
| Budesonide | 0.5 mg to 2 mg |
| CMC and MCC (e.g., Avicel RC-591) | 0.01 g to 0.3 g |
| Dextrose | 0.1 g to 1 g |
| Maltodextrin | 0.5 g to 2 g |
| EDTA (e.g., disodium edetate) | 1 mg to 10 mg |
| Citric Acid | 0.1 mg to 100 mg |
| Citrate (e.g., sodium citrate) | 0.1 mg to 200 mg |
| Polysorbate 80 (e.g., Tween 80) | 0.1 mg to 10 mg |
| Cherry Flavor | 1 mg to 100 mg |
| Sweetener | 100 mg to 1 g |
| Sodium Benzoate | 1 mg to 50 mg |
| Potassium Sorbate | 1 mg to 50 mg |
| Water | q.s. to 5 mL |

TABLE 5

Budesonide Composition #5

| Ingredient | Amount |
| --- | --- |
| Budesonide | 0.5 mg to 2 mg |
| CMC and MCC (e.g., Avicel RC-591) | 0.02 g to 0.6 g |
| Dextrose | 0.2 g to 2 g |
| Maltodextrin | 1 g to 4 g |
| EDTA (e.g., disodium edetate) | 2 mg to 20 mg |
| Citric Acid | 0.2 mg to 200 mg |
| Citrate (e.g., sodium citrate) | 0.2 mg to 400 mg |
| Polysorbate 80 (e.g., Tween 80) | 0.2 mg to 20 mg |
| Cherry Flavor | 2 mg to 200 mg |
| Sweetener | 200 mg to 2 g |
| Sodium Benzoate | 2 mg to 100 mg |
| Potassium Sorbate | 2 mg to 100 mg |
| Water | q.s. to 10 mL |

TABLE 6

Budesonide Composition #6

| Ingredient | Amount (mg/mL) |
| --- | --- |
| Budesonide | 0.01 to 0.5 |
| CMC and MCC (e.g., Avicel RC-591) | 2 to 100 |
| Dextrose | 10 to 500 |
| Maltodextrin (M150) | 10 to 500 |
| EDTA (e.g., disodium edetate) | 0.01 to 10 |
| Citric acid | 0.1 to 10 |
| Citrate (e.g., sodium citrate) | 0.1 to 10 |
| Polysorbate 80 (e.g., Tween 80) | 0.01 to 1 |
| Flavoring agent (e.g., Cherry Flavor) | 0.1 to 100 |
| Glycerin | 10 to 100 |
| Acesulfame potassium | 0.1 to 40 |
| Magnasweet 110 | 0.1 to 40 |
| Sodium Benzoate | 0.1 to 10 |
| Potassium Sorbate | 0.1 to 10 |
| Water | q.s. to 1-15 mL |

TABLE 7

Budesonide Composition #7

| Ingredient | Amount (mg/mL) |
| --- | --- |
| Budesonide | about 0.05 to about 0.2 |
| CMC and MCC (e.g., Avicel RC-591) | 5 to 50 |
| Dextrose | 50 to 250 |
| Maltodextrin (M150) | 200 to 500 |
| EDTA (e.g., disodium edetate) | 0.1 to 1 |
| Citric acid | 0.5 to 5 |
| Citrate (e.g., sodium citrate) | 0.2 to 2 |
| Polysorbate 80 (e.g., Tween 80) | 0.01 to 0.4 |
| Flavoring agent (e.g., Cherry Flavor) | 1 to 10 |
| Glycerin | 30 to 80 |
| Acesulfame potassium | 1 to 10 |
| Magnasweet 110 | 1 to 10 |
| Sodium Benzoate | 0.5 to 4 |
| Potassium Sorbate | 0.5 to 4 |
| Water | q.s. to 1-15 mL |

TABLE 8

Budesonide Composition #8

| Ingredient | Amount (mg/mL) | Amount % w/w |
| --- | --- | --- |
| Budesonide | 0.05 | 0.004 |
| Avicel RC-591 | 23.6 | 2 |
| Dextrose | 118 | 10 |
| Maltodextrin (M150) | 306.8 | 26 |
| Disodium edetate | 0.59 | 0.05 |
| Citric acid | 1.77 | 0.15 |
| Sodium citrate | 0.59 | 0.05 |
| Polysorbate 80 | 0.12 | 0.01 |
| Cherry Flavor | 5.9 | 0.5 |
| Glycerin | 59 | 5 |
| Acesulfame potassium | 5.9 | 0.5 |
| Magnasweet 110 | 5.9 | 0.5 |
| Sodium Benzoate | 2.36 | 0.2 |
| Potassium Sorbate | 2.36 | 0.2 |

TABLE 8-continued

Budesonide Composition #8

| Ingredient | Amount (mg/mL) | Amount % w/w |
|---|---|---|
| Water | q.s. to 1, 2, 3, 4, 5, 6, 7, 8, 9, 10, 11, 12, 13, 14, or 15 mL | q.s. to 1, 2, 3, 4, 5, 6, 7, 8, 9, 10, 11, 12, 13, 14, or 15 mL |

TABLE 9

Budesonide Composition #9

| Ingredient | Amount (mg/mL) | Amount % w/w |
|---|---|---|
| Budesonide | 0.2 | 0.17 |
| Avicel RC-591 | 23.6 | 2 |
| Dextrose | 118 | 10 |
| Maltodextrin (M150) | 306.8 | 26 |
| Disodium edetate | 0.59 | 0.05 |
| Citric acid | 1.77 | 0.15 |
| Sodium citrate | 0.59 | 0.05 |
| Polysorbate 80 | 0.12 | 0.01 |
| Cherry Flavor | 5.9 | 0.5 |
| Glycerin | 59 | 5 |
| Acesulfame potassium | 5.9 | 0.5 |
| Magnasweet 110 | 5.9 | 0.5 |
| Sodium Benzoate | 2.36 | 0.2 |
| Potassium Sorbate | 2.36 | 0.2 |
| Water | q.s. to 1, 2, 3, 4, 5, 6, 7, 8, 9, 10, 11, 12, 13, 14, or 15 mL | q.s. to 1, 2, 3, 4, 5, 6, 7, 8, 9, 10, 11, 12, 13, 14, or 15 mL |

TABLE 10

Fluticasone Propionate Composition #1

| Ingredient | Amount |
|---|---|
| Fluticasone Propionate | 0.5 mg to 150 mg |
| CMC, MCC, Carbomer, HPMC and/or HEC | 0.5 g to 10 g |
| Dextrose | 0 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 11

Fluticasone Propionate Composition #2

| Ingredient | Amount |
|---|---|
| Fluticasone Propionate | 0.5 mg to 150 mg |
| CMC, MCC, Carbomer, HPMC and/or HEC | 0 g to 10 g |
| Dextrose | 1 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 12

Fluticasone Propionate Composition #3

| Ingredient | Amount |
|---|---|
| Fluticasone Propionate | 0.5 mg to 150 mg |
| CMC, MCC, Carbomer, HPMC and/or HEC | 0 g to 10 g |
| Dextrose | 0 g to 100 g |
| Maltodextrin | 1 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

Diseases

In some embodiments, provided herein are methods of treating, preventing, or alleviating inflammation or symptoms associated with inflammation of the gastrointestinal tract, e.g., the esophagus. In specific embodiments, the method provided herein is a method of reducing or alleviating symptoms of inflammation of the gastrointestinal tract. In more specific embodiments, the inflammation of the gastrointestinal tract is eosinophilic esophagitis (EoE). In some embodiments, the method provided herein is a method of treating inflammation associated with eosinophilic esophagitis (EoE). In certain embodiments, the method provided herein is a method of treating dysphagia associated with eosinophilic esophagitis (EoE). In some embodiments, the method provided herein is a method of treating inflammation and dysphagia associated with eosinophilic esophagitis (EoE). In certain embodiments, provided herein are methods of treating diseases or conditions of the gastrointestinal tract (e.g., a disease or condition of the upper gastrointestinal tract, including a disease or condition of the esophagus), by administering a composition described herein.

In some embodiments, administration of the composition described herein treats, prevents, or alleviates inflammation or symptoms associated with the inflammatory disease or condition. Diseases or conditions of the gastrointestinal tract include, by way of non-limiting example, any chronic inflammatory or malignant state that involves the gastrointestinal tract (e.g., the upper gastrointestinal tract, esophagus, stomach and/or digestive tract) and responds to steroid therapy. In certain instances) the diseases or conditions treated by the compositions described herein include diseases or conditions of the upper gastrointestinal tract (including pre-colonic disease and disorders), the esophagus, the stomach, and/or the digestive tract. The methods of the present invention are useful, for example, for treating, preventing and alleviating the inflammation associated with or symptoms of eosinophilic esophagitis, inflammatory bowel diseases involving the esophagus, Crohn's disease, acute esophageal inflammation secondary to caustic/irritant ingestion, persistent/recurrent esophageal strictures secondary to caustic/irritant, conditions due to ingestion, systemic diseases, congenital diseases, post-surgery inflammation, and gastro enteritis. The methods of the present invention are also useful, for example, for treating, preventing and alleviating inflammation associated with or symptoms of gastroesophageal reflux disease (GERD), nonerosive reflux disease (NERD), Barrett's Esophagus, and/or erosive esophagitis.

It will be appreciated that reference herein to treatment extends to prophylaxis as well as the treatment of inflammation or other symptoms.

In certain embodiments, provided herein is a method of treating, preventing or alleviating inflammation of the gastrointestinal tract, including, by way of non-limiting example, the esophagus, stomach and/or digestive tract, in an individual comprising orally administering to said individual any of the compositions described herein. In certain embodiments, the oral dosage form comprises a liquid vehicle and is formulated as, e.g., a slurry, suspension, syrup, dispersion, solution, etc.

In one aspect, a patient is administered a corticosteroid such as, for example, budesonide or fluticasone propionate.

In some embodiments, the inflammation treated by the methods and compositions described herein is associated with eosinophilic inflammation and/or neutrophilic inflammation. In some embodiments, individuals (e.g., patients) to be treated with compositions described herein include those that have been diagnosed with eosinophilic esophagitis, an inflammatory bowel disease involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., *Candida*, turolopsis, histoplasma *Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, or gastro enteritis. In one non-limiting example, the patient has eosinophilic esophagitis. In some embodiments, individuals (e.g., patients) to be treated with the compositions described herein include those that have been diagnosed with Barrett's Esophagus, gastroesophageal reflux disease (GERD), nonerosive reflux disease (NERD) and/or erosive esophagitis. In some embodiments, the patient is an adult. In other embodiments, the patient is a child or infant. In various aspects, a patient is a child or infant less than 16 years old, less than 12 years old, less than 8 years old, less than 6 years old, less than 4 years old or less than 2 years old.

In some embodiments, a composition is in a unit dose formulation for oral administration of a patient. In some embodiments, a unit dose of the corticosteroid is administered from a metered dose device. In some embodiments, the metered dose device delivers a metered unit dose of a composition described herein to the mouth or throat of an individual in need thereof. In certain embodiments, the metered dose device is a metered inhaler, which is utilized to administer a metered unit dose to the mouth or throat of an individual (the individual swallows rather than inhales the metered unit dose). In certain embodiments, a metered dose device dispenses a metered unit dose of a composition described herein into a receptacle (e.g., a cup), which is then utilized to orally administer the metered unit dose to the mouth or throat. In certain aspects, about 0.01 mg to about 20 mg, about 0.01 mg to about 15 mg, or about 0.01 mg to about 10 mg (e.g., about 0.1-10 mg, about 0.25-5 mg, about 0.3-4 mg, about 0.25-2.5 mg, about 1-2 mg or about 2-3 mg) corticosteroid per day or per dose is administered to an individual. In some embodiments, the corticosteroid is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg). In some embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, or between about 2 and about 3 mg.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these publications or documents.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies which are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

In some embodiments, provided herein is a multiple unit container comprising about 2 to about 180, about 10 to about 60, about 14, or about 30 unit doses of any pharmaceutical composition described herein. In more specific embodiments, each dose comprises about 1 mL to about 25 mL, about 1 mL to about 20 mL, about 7 mL to about 25 mL, about 10 to about 20 mL, about 15 mL, about 20 mL, about 3 to about 7 mL, about 5 nm, about 8 mL to about 12 mL, or about 10 mL. In still more specific embodiments, each dose comprises about 0.1 to about 20 mg, about 0.1 to about 10 mg, about 0.1 to about 7.5 mg, about 0.1 to about 5 mg, about 0.3 to about 4 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg of corticosteroid. In certain embodiments, provided herein is a multiple unit container comprising about 10 mL to about 1500 mL, about 50 mL to about 600 mL, about 150 mL, about 300 mL, about 600 mL, or about 1,200 mL of any pharmaceutical composition described herein. In specific embodiments, the multidose container comprises about 330 mL or about 55 mL of a composition described herein. In some embodiments, a kit provided herein comprises any multidose container as described herein, a pharmaceutical composition as described herein (e.g., in a volume described), and a delivery device (e.g., a syringe, a cup, a spoon, or the like). In specific embodiments, the delivery device is incorporated into the container (e.g., an nebulizer, a aerosolizer, a pump, or the like). In certain embodiments, the pharmaceutical composition contained within any of the multiple unit containers described herein is physically and chemically stable.

In certain aspects, about 0.1 mg to about 20 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.3 mg to about 4 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) corticosteroid per day is administered to a patient. In some embodiments, the corticosteroid is present in a unit dose in an amount of between about 0.25 mg and about 5 mg. In some embodiments, the amount of corticosteroid administered daily or in a unit dose is between about 0.3 mg and about 4 mg. In certain embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, or between about 2 and about 3 mg.

In some embodiments, any composition or formulation described herein is stable. In specific embodiments, the composition is chemically and physically stable. In certain embodiments, chemical stability is evidenced by a composition that comprises at least 80%, 90%, 95%, 98%, or 99% of the initial amount or label amount of corticosteroid and/or optional additional active agent therein for, by way of non-limiting example, 1 week, 2 weeks, 3 weeks, 1 month, 3 months, 6 months, 1 year, 2 years, or for the duration of the shelf life. In some embodiments, physical stability is evidenced by a pharmaceutical composition that is able to substantially obtain uniformity, remain substantially uniform (e.g., for at least 1 day, 3 days, 1 week, 2 weeks, 3 weeks, 1 month, 3 months, 6 months, 1 year, 2 years, etc.), or substantially regain uniformity (e.g., via mild or moderate agitation after being undisturbed for 1 day, 3 days, 1 week, 2 weeks, 3 weeks, 1 month, 3 months, 6 months, 1 year, 2 years, etc.). In certain embodiments, physical stability is evidenced by a composition that comprises at least 80%, 90%, 95%, 98%, or 99% of the initial amount or label amount of corticosteroid and/or optional additional active agent therein for, by way of non-limiting example, 2 days, 1 week, 2 weeks, 3 weeks, 1 month, 3 months, 6 months, 1 year, 2 years, or for the duration of the shelf life. In certain embodiments, uniformity as described herein is evidenced by the uniformity of the dispersion of the corticosteroid particles throughout the pharmaceutical composition, the uniformity of the dispersed mass of corticosteroid throughout the pharmaceutical composition, the uniformity of the concentration of one or more of the components in the composition throughout the pharmaceutical composition, and the like. In certain embodiments, mild or moderate agitation includes, by way of non-limiting example, shaking, shaking well, swirling, gentle swirling, and the like.

In some embodiments, mild or moderate agitation includes agitation without a special apparatus. In some embodiments, uniformity of the pharmaceutical composition refers to dose uniformity (e.g., each dose delivered or withdrawn from the composition comprises a substantially similar amount of corticosteroid), or the concentration of corticosteroid in at least some or all of the doses from the multiple dose formulations are substantially similar. In certain embodiments, substantially similar includes, e.g., within 20%, 15%, 10%, 7%, 5%, 3%, 2%, or 1%.

In some embodiments, the dose or volume of a composition administered herein is adjusted based on the efficacy of treatment. In certain embodiments, a diagnosis of eosinophilic esophagitis is achieved by administering a composition described herein and determining the efficacy of the treatment. In certain embodiments, a composition described herein and separately determined to be effective in treating eosinophilic esophagitis is utilized. Efficacy of treatment can be determined in any suitable manner including, e.g., symptom score assessment, gastrointestinoscopy (e.g., esophagogastroduodenoscopy), gastrointestinal (e.g., esophageal) biopsy, histological evaluation, or a combination thereof. Processes of diagnosing eosinophilic esophagitis and/or determining efficacy of treatment include any suitable process including, by way of non-limiting example, processes as set forth in Aceves et al, J Allergy Clin Immunol, February 2008; abstract 270, or Aceves et al, Am J Gastroenterol., October 2007, 102 (10):2271-9, both of which are incorporated herein in their entirety.

In some embodiments, a process for determining efficacy of a treatment (e.g., for eosinophilic esophagitis) described herein is a clinical symptom score assessment comprising (i) administering a composition described herein to an individual diagnosed with or suspected of having eosinophilic esophagitis; and (ii) evaluating one or more symptom of the individual. Symptoms that are optionally scored include, by way of non-limiting example, nausea, vomiting, pain, and heartburn. Total score or change in score is optionally utilized to diagnose a disorder and/or determine efficacy of treatment.

In certain embodiments, a process for determining efficacy of a treatment described herein comprises (i) administering a composition described herein to an individual diagnosed with or suspected of suffering from inflammation of the gastrointestinal tract (e.g., eosinophilic esophagitis) and/or symptoms associated therewith; (ii) endoscoping the gastrointestinal surface of the individual; (iii) biopsying the gastrointestinal surface tissue; and (iv) evaluating the biopsied tissue and optionally determining an endoscopy score of the tissues biopsied. In specific embodiments, the process further comprises comparing the evaluated biopsied tissue and/or the endoscopy score obtained prior to administration of the composition to the biopsied tissue and/or endoscopy score subsequent to administration of the composition.

In some embodiments, provided herein is a process of diagnosing an individual with gastrointestinal inflammation by (i) detecting and/or measuring symptoms of the individual prior to administering to the individual a composition described herein; (ii) administering to the individual any composition described herein; (iii) detecting and/or measuring symptoms of the individual following administration of the composition; and (iv) comparing the symptoms measured or detected prior to and following administration of a composition described herein. If the symptoms exhibited by the individual are reduced (e.g., by a statistically significant or clinically relevant amount), a positive diagnosis occurs. In specific embodiments, the process of diagnosing an individual with gastrointestinal inflammation is diagnosing an individual with eosinophilic esophagitis.

Combinations

As discussed herein, compositions and formulations described comprise at least one corticosteroid (e.g., budesonide or fluticasone propionate). In some embodiments, a composition or formulation described herein further comprises at least one additional active agent. In specific embodiments, a composition or formulation described herein comprises a therapeutically effective amount of a corticosteroid and a therapeutically effective amount of at least one additional active agent. In some embodiments, the at least one additional active agent is an agent that treats, prevents, or alleviates the symptoms of and/or inflammation associated with inflammatory diseases involving the gastrointestinal tract (e.g., esophagus). It is to be understood that in certain instances, when the corticosteroid is combined with an additional active agent, the therapeutically effective amount of the corticosteroid is less than it when the additional active agent is absent.

Furthermore, provided herein are methods of preventing or alleviating gastrointestinal (e.g., esophageal) inflammation in an individual comprising orally administering to the individual a corticosteroid in association or combination with at least one additional active agent. In certain embodiments, the corticosteroid and the at least one additional active agent is in a single dosage form. In other embodiments, the corticosteroid and the at least one additional active agent are in separate dosage forms and are administered in any manner, including, by way of non-limiting example, simultaneously, sequentially, or at different times. For example, in certain embodiments, several doses of a corticosteroid composition are administered over a period of time, after which administration of the corticosteroid composition is discontinued and administration of at least one additional active agent is administered at least once.

In some embodiments, the at least one additional active agent utilized in a composition, formulation or method described herein is an agent that treats, prevents, or alleviates the symptoms of and/or inflammation associated with inflammatory diseases involving the gastrointestinal tract (e.g., esophagus). In more specific embodiments, the at least one additional active agent is not a second corticosteroid. In certain embodiments, the at least one additional active agent is an acid inhibitor (e.g., an H2 antagonist and/or a PPI). In certain embodiments, the at least one additional active agent is, by way of non-limiting example, a proton pump inhibitor (PPI), a H2 antagonist, a transient lower esophageal sphincter relaxation (TLESR)-reducing agent, a serotonergic agent/prokinetics, a potassium-competitive acid blocker (P-CAB), a mucosal protectant, a histamine H3 agonist, an anti-gastrin agent, or combinations thereof.

In certain embodiments, a patient combines treatment with a composition described herein with a treatment with another medication, and/or dietary therapy.

EXAMPLES

Example 1

This example illustrates the increased interaction between a composition described herein and the esophagus when compared to a radiolabeled oral composition made by combining Pulmicort Respules® (4 mL) with $^{99m}$Tc pertechnetate, and diluting with saline to about 7-8 mL (M0). The M0 composition has a viscosity of about 1 cP at 13.2 sec$^{-1}$. Administered to a population of healthy individuals was a radiolabeled oral budesonide composition (M1). The radiolabeled budesonide composition (M1) was made in a volume of about 7-8 mL by combining Pulmicort Respules®, about 10 packets of Splenda® (distributed by McNeil Nutritionals, LLC Fort Washington, Pa. 19034-2299), and $^{99m}$Tc pertechnetate, comprises about 7% w/w maltodextrin, and has a viscosity of about 200 cP at 13.2 sec$^{-1}$. The radiolabeled budesonide composition (M2) was made in a volume of about 7-8 mL by combining Pulmicort Respules®, 70% w/w maltodextrin, and $^{99m}$Tc pertechnetate, having a viscosity of about 1450 cP at 13.2 sec$^{-1}$. Also administered to a population of healthy individuals was a radiolabeled budesonide composition (Rhinocort Aqua®, M3), which has a viscosity of about 39 at 13.2 sec$^{-1}$. Increased interaction of the budesonide composition was determined by measuring the amount of radiolabel present in the esophagus following oral administration of the oral viscous budesonide composition. FIG. 1 illustrates the percent amount of composition present in the esophagus as a function of time following oral administration (by measuring the amount of radiolabel present in the esophagus).

The area under the curve (AUCr) of the percent of the dose administered as a function of time (% dose·time (min)) was determined from the time of 50% swallow (i.e., 50% of the administered dose had passed from the mouth), until esophageal activity had peaked and fallen to 10% of the peak value. The area under the curve from t=0 min to t=1 min (AUC$_{0-1}$); and from t=0 min to t=2 min (AUC$_{0-2}$) was also determined. These results (including the ratio of the non-viscous sample to the viscous sample) are set forth below:

| Formulation | AUCr geometric mean | ratio | AUC$_{0-1}$ geometric mean | ratio | AUC$_{0-2}$ geometric mean | ratio |
|---|---|---|---|---|---|---|
| M0 | 3.95 | | 5.51 | | 6.93 | |
| M1 | 6.33 | 0.62 | 8.84 | 0.62 | 9.41 | 0.74 |
| M2 | 17.67 | 0.22 | 18.91 | 0.29 | 21.94 | 0.32 |
| M3 | 9.39 | 0.42 | 11.07 | 0.5 | 14.16 | 0.49 |

Example 2

This example details the efficacy and safety of once daily and twice daily use of budesonide in a formulation described herein in 5 mL and 7 mL doses in inducing and maintaining remission of disease activity in children with EE. A number of children (e.g., 20 per budesonide dose frequency, amount, and volume) are evaluated to determine the highest eosinophil count (eos/hpf) and the mean highest eosinophil count for the group. Evaluation of the highest eosinophil count (eos/hpf) and the mean highest eosinophil count for the group is also determined following therapy. Symptom scores and mean symptom scores are also determined before and after therapy.

In some instances, individuals who received previous therapy with proton pump inhibitor, elimination diet based upon skin or blood allergy testing, or elimination diet or refused elimination diet, but continued to have ≥24 eos/hpf on esophageal biopsy are included in the review. Patients are defined as having food or aeroallergen sensitization if RAST and/or skin prick testing are positive. No changes are made to longstanding therapy used for treating chronic conditions such as asthma or eczema and none of the children receive concurrent immune-modulatory treatment.

Endoscopy is performed using the Olympus P160 endoscope (by RD) and pan-esophageal, gastric and duodenal biopsies are taken. Eosinophilic esophagitis is diagnosed when ≥24 eos/hpf are found in at least one of the esophageal sites biopsied. Two mucosal biopsies are taken from the proximal esophagus (3 cm below the crycopharyngeus muscle), distal esophagus (3 cm above the gastroesophageal junction (GEJ), and mid-esophagus (midpoint between the crycopharyngeus muscle and the GEJ). Biopsies are processed routinely and evaluated by a pediatric pathologist (RN). The highest number of eosinophils per ×400 high power field are counted. Basal zone hyperplasia (BZH) is reported when basal zone cells extend towards the luminal surface of the epithelium (>25% of epithelial thickness).

Follow-up endoscopy with biopsies are taken after 3-4 months treatment. Counting the highest number of eos/hpf within biopsies determined the response to therapy and patients are categorized into responders (0-7 eos/hpf), partial-responders (8-23 eos/hpf) and non-responders (≥24 eos/hpf).

An EE (EoE) Endoscopy Score is devised to compare findings before and after treatment. It is calculated from procedure reports and photographs. Four categories, (U) pallor and diminished vascular markings; (2) furrowing with "thickened" mucosa; (3) white mucosal plaques; (4) concentric rings or strictures. For each category, one point is allocated if 1 or 2 esophageal sites are involved, and two points for pan-esophageal involvement. The maximum score is 8.

Patients receive a formulation described herein for between 0.25 and 2 mg daily and are instructed not to ingest any solids or liquids for 30 minutes afterwards. No dietary changes are made in patients already on dietary restrictions.

A modified symptom score based on children with acid-peptic disease is used routinely in the EE (EoE) clinic. The symptom categories include (1) heartburn or regurgitation; (2) abdominal pain or unexplained irritability in younger children; (3) nausea or vomiting; (4) anorexia or early satiety; (5) dysphagia or odynophagia, (6) nocturnal wakening with symptoms; (7) gastrointestinal bleeding (previous 4 months). Each category scored 0-2 points with a maximum of 14 points. Zero points are awarded if the symptom is absent; one point if the symptom is mild, did not interfere with daily activities; 2 points if the symptoms are severe enough to interrupt daily activities. Previous GI bleeding is considered mild (1 point) if there is no associated hemodynamic compromise or anemia, and severe (2 points) if bleeds are multiple, caused anemia, or required blood transfusion.

All statistical analysis is carried out using NCSS Statistical Software Package. Two-tailed p values are calculated using paired t-tests to compare the means of patient values for eos/hpf, EE (EoE) Endoscopy Scores and Symptom Scores before and after budesonide therapy. Two-tailed unpaired t-tests are utilized in order to compare variables grouped by responders versus non-responders. Spearman's correlation coefficients are generated using GraphPad Prism software. Results with p values <0.05 are considered statistically significant. Both mean and median statistics are generated, both are equivalent and mean statistics are presented.

Subjects. Chart reviews are undertaken on a number of children. All children have >24 eos/hpf on repeat esophageal biopsy before starting therapy.

Treatment. Patients received the described formation for a designated amount of time (e.g., 1 week, 2 weeks, 1 month, 2 months, 3 months, 4 months, 6 months, or the like) before repeat endoscopy. Various patients received budesonide in amounts ranging from 0.25 to 2 mg/day.

Histology. Before treatment the mean highest eosinophil count is measured for all patients, including distal, mid and proximal esophageal sites. All sites are likewise evaluated aver the designated amount of time, and again if desired.

Upper Gastrointestinal Endoscopy. Before treatment, the mean EE (EoE) Endoscopy Score for all patients is determined. Following treatment the mean EE (EoE) Endoscopy Score is repeated. Decreases in endoscopy scores (e.g., of >95%, >90%, >85%, >75%, >50%, >25%, or the like) in an individual indicate successful treatment.

Symptom Score. Before treatment the mean symptom score for all patients is determined. It is again determined following treatment. Decreases in symptom scores (e.g., of >95%, >90%, >85%, >75%, >50%, >25%, or the like) in an individual indicate successful treatment (alone or in combination with the above referenced decreases in endoscopy scores).

Adults: these parameters are repeated in adults to determine efficacy and safety therein.

Example 3

This example details the efficacy and safety of once daily and twice daily use of budesonide in a formulation described herein in inducing and maintaining remission of disease activity in individuals (children and/or adults) with GERD. Doses of 0-1 mg, 1-2 mg, 2-3 mg, 3-4 mg, 4-5 mg, and 5-6 mg per daily dose are administered once a day, b.i.d. or t.i.d. in volumes of 3, 5, 7, 10, 12, 15, or 17.5 mL. A number of individuals (e.g., 20 per budesonide dose frequency, amount, and volume) are evaluated to determine the symptoms prior to therapy, during therapy and following therapy. Administration is conducted for 7 days, 14 days, and 28 days. Primary Outcome Measures include complete resolution of heartburn and regurgitation (e.g., no more than one day with either mild heartburn or regurgitation over the seven days prior to the assessment time-point). Secondary Outcome Measures include: Number of days with heartburn (daytime and night-time); Number of days with regurgitation (daytime and night-time); Number of heartburn and regurgitation-free days (24 hrs); Composite score of heartburn and regurgitation frequency and severity; Time to resolution of symptoms of heartburn/regurgitation; Severity of additional GERD symptoms; Quality of Life (assessed using PAGI-QOL to PGIC (Patient Global Impression of Change); Complete resolution of heartburn; Complete resolution of regurgitation; Average severity of heartburn (daytime and night-time); Average severity of regurgitation (daytime and night-time). These symptoms are scored (e.g., assigning a 3 to the most severe symptoms and a 0 to a lack of symptoms) and utilized to determine the efficacy of the treatment.

While certain embodiments have been shown and described herein, it will be apparent to those skilled in the art that such embodiments are provided by way of example only. Numerous variations, changes, and substitutions will now occur to those skilled in the art and are considered to be within the scope of the disclosure herein. It should be understood that various alternatives to the embodiments of the invention described herein may be employed in practicing the invention. It is intended that the following claims define the scope of the invention and that methods and structures within the scope of these claims and their equivalents be covered thereby.

References

1. Liacouras C A, Ruchelli E. Eosinophilic esophagitis. Cuff. Opin. Pediatr. 2004; 16:560-6.

2. Kelly K J, Lazenby A J, Rowe P C, et al. Eosinophilic esophagitis attributed to gastroesophageal reflux: improvement with an amino acid-based formula. Gastroenterology 1995; 109: 1503-12.

3. Fogg M I, Ruchelh E, Spergel J M. Pollen and eosinophilic esophagitis. J. Allergy Clin. Immunol. 2003; 112:796-7.

4. Mishra A, Hogan S P, Brandt E B, Rothenberg M E. An etiological role for aeroallergens and eosinophils in experimental esophagitis. J. Clin. Invest. 2001; 107:83-90.

5. Spergel J M, Beausoleil J L, Mascarenhas M, Liacouras C A. The use of skin prick tests and patch tests to identify causative foods in eosinophilic esophagitis. J. Allergy Clin. Immunol. 2002; 109:363-8.

6. Ruchelli E, Wenner W, Voytek T, et al. Severity of esophageal eosinophilia predicts response to conventional gastroesophageal reflux therapy. Pediatr. Dev. Pathol. 1999; 2:15-8.

7. Steiner S J, Gupta S K, Croffie J M, Fitzgerald J F. Correlation between number of eosinophils and reflux index on same day esophageal biopsy and 24 hour esophageal pH monitoring. Am. J. Gastroenterol. 2004; 99:801-5.

8. Orenstein S R, Shalaby T M, Di Lorenzo C, et al. The spectrum of pediatric eosinophilic esophagitis beyond infancy: a clinical series of 30 children. Am. J. Gastroenterol. 2000; 95:1422-30.

9. Rothenberg M E, Mishra A, Collins M H, Putnam P E. Pathogenesis and clinical features of eosinophilic esophagitis. J. Allergy Clin. Immunol. 2001; 108:891-4.

10. Ravelli A M, Villanacci V, Ruzzenenti N, et al. Dilated Intercellular Spaces: A Major Morphological Feature of Esophagitis. J. Pediatr. Gastroenterol. Nutr. 2006; 42:510-515.

11. Steiner S J, Kernek K M, Fitzgerald J F. Severity of Basal Cell Hyperplasia Differs in Reflux Versus Eosinophilic Esophagitis. J. Pediatr. Gastroenterol. Nutr. 2006; 42:506-509.

12. Mueller S, Aigner T, Neureiter D, Stolte M. Eosinophil infiltration and degranulation in oesophageal mucosa from adult patients with eosinophilic oesophagitis: a retrospective comparative study on pathologic biopsy. J. Clin. Pathol. 2006; 59:1175-80.

13. Croese J, Fairley S K, Masson J W, et al. Clinical and endoscopic features of eosinophilic esophagitis in adults. Gastrointest. Endosc. 2003; 58:516-22.

14. Aceves S, Newbury, R O, Dohil R, Schwimmer J, Bastian J. Distinguishing Eosinophilic Esophagitis in pediatric patients: clinical, endoscopic, and histologic features of an emerging disorder. Journal of Clinical Gastroenterology 2006; 41 (3):252-6.

15. Straumann A, Simon H U. Eosinophilic esophagitis: escalating epidemiology? J. Allergy Clin. Immunol. 2005; 115:418-9.

16. Cherian S, Smith N M, Forbes D A. Rapidly increasing prevalence of eosinophilic oesophagitis in Western Australia. Arch. Dis. Child 2006; 91:1000-4.

17. Sant'Anna A M, Rolland S, Fournet J C, et al. Eosinophilic Esophagitis in Children: Symptoms, Histology and pH Probe Results. J. Pediatr. Gastroenterol. Nutr. 2004; 39:373-377.

18. Potter J W, Sacian K, Staff D, et al. Eosinophilic esophagitis in adults: an emerging problem with unique esophageal features. Gastrointest. Endosc. 2004; 59:355-61.

19. Parfitt J R, Gregor J C, Suskin N G, et al. Eosinophilic esophagitis in adults: distinguishing features from gastroesophageal reflux disease: a study of 41 patients. Mod. Pathol. 2006; 19:90-6.

20. Desai T K, Stecevic V, Chang C H, et al. Association of eosinophilic inflammation with esophageal food impaction in adults. Gastrointest. Endosc. 2005; 61:795-801.

21. Straumanm A, Spichtin H P, Grize L, et al. Natural history of primary eosinophilic esophagitis: a follow-up of 30 adult patients for up to 11.5 years. Gastroenterology 2003; 125:1660-9.

22. Spergel J M, Andrews T, Brown-Whitehorn T F, et al. Treatment of eosinophilic esophagitis with specific food elimination diet directed by a combination of skin prick and patch tests. Ann. Allergy Asthma Immunol. 2005; 95:336-43.

23. Kagalwalla A F, Sentongo T A, Ritz S, et al. Effect of six-food elimination diet on clinical and histologic outcomes in eosinophilic esophagitis. Clin. Gastroenterol. Hepatol. 2006; 4:1097-102.

24. Markowitz J E, Spergel J M, Ruchelli E, Liacouras C A. Elemental diet is an effective treatment for eosinophilic esophagitis in children and adolescents. Am. J. Gastroenterol. 2003; 98:777-82.

25. Liacouras C A, Wenner W J, Brown K, Ruchelli E. Primary eosinophilic esophagitis in children: successful treatment with oral corticosteroids. J. Pediatr. Gastroenterol. Nutr. 1998; 26:380-5.

26. Teitelbaum J E, Fox V L, Twarog F J, et al. Eosinophilic esophagitis in children: immunopathological analysis and response to fluticasone propionate. Gastroenterology 2002; 122:1216-25.

27. Faubion W A, Jr., Perrault J, Burgart L J, et al. Treatment of eosinophilic esophagitis with inhaled corticosteroids. J. Pediatr. Gastroenterol. Nutr. 1998; 27:90-3.

28. Aceves S S, Dohil R, Newbury R O, Bastian J F. Topical viscous budesonide suspension for treatment of eosinophilic esophagitis. J. Allergy Clin. Immunol. 2005; 116:705-6.

29. Noel R J, Putnam P E, Collins M H, et al. Clinical and immunopathologic effects of swallowed fluticasone for eosinophilic esophagitis. Clin. Gastroenterol. Hepatol. 2004; 2:568-75.

30. Remedios M, Campbell C, Jones D M, Kerlin P. Eosinophilic esophagitis in adults: clinical, endoscopic, histologic findings, and response to treatment with fluticasone propionate. Gastrointest. Endosc. 2006; 63:3-12.

31. Dohil R, Newbury R O, Sellers Z M, et al. The evaluation and treatment of gastrointestinal disease in children with cystinosis receiving cysteamine. J. Pediatr. 2003; 14:224-30.

32. Cheung K M, Oliver M R, Cameron D J, et al. Esophageal eosinophilia in children with dysphagia. J. Pediatr. Gastroenterol. Nutr. 2003; 37:498-503.

33. Fox V L, Nurko S, Furuta G T. Eosinophilic esophagitis: it's not just kid's stuff. Gastrointest. Endosc. 2002; 56:260-70

34. Budin C, Villard-Truc F, Rivet C, et al. [Eosinophilic esophagitis: 3 case reports]. Gastroenterol. Clin. Biol. 2005; 29:73-5.

35. Noel R J, Putnam P E, Rothenberg M E. Eosinophilic esophagitis. N. Engl. J. Med. 2004; 351:940-1.

36. Guajardo J R, Plotnick L M, Fende J M, et al. Eosinophil-associated gastrointestinal disorders: a world-wide-web based registry. J. Pediatr. 2002; 141:576-81.

37. Liacouras C A, Spergel J M, Ruchelli E, et al. Eosinophilic esophagitis: a 10-year experience in 381 children. Clin. Gastroenterol. Hepatol. 2005; 3:1198-206.

38. Liacouras C A. Eosinophilic esophagitis: treatment in 2005. Curr. Opin. Gastroenterol. 2006; 22:147-152.

39. Spergel J M. Eosinophilic esophagitis in adults and children: evidence for a food allergy component in many patients. Curr. Opin. Allergy Clin. Immunol. 2007; 7:274-8.

40. Plaza-Martin, A M, Jimenez-Feijoo R, Andaluz C, Giner-Munoz M T, Martin-Mateos M A, Piquer-Gibert M, Sierra-Martinez J I. Polysensitization to aeroallergens and food in eosinophilic esophagitis in a pediatric population. Alergol. Immunopathol. 2007; 35:35-7.

41. Nicolazzo, J A, Reed, B L, Finnin, B C. Buccal penetration enhancers—how do they really work? J. Controlled Release 2005; 105:1-15.

42. Furuta, G T, Liacouras, C A, Collins, M H, Sandeep, K G, Justinich, C, Putnam, P E, Bonis, P, Hassall, E, Straumann, A, Rothenberg, M E. Eosiniophilic esophagitis in children and adults: A systematic review and consensus recommendations for diagnosis and treatment. Gastroenterology 2007; 133:1342-1363.

43. Aceves, S S, Bastian J F, Newbury, R O, Dohil, R. Oral viscous budesonide: A potential new therapy for eosinophilic esophagitis. Amer. Journal of Gastroenterology 2007; 102:1-9.

44. Rothenberg M E. Eosinophilic gastrointestinal disorders. J. Allergy Clin. Immunol. 2004; 113:11-28.

45. Garrett J K, Jameson S C, Thomson B, Collins M H, Wagoner L E, Freese, D K, et al. Anti-interleukin-5 (mepolizumab) therapy for hypereosinophilic syndromes. J. Allergy Clin. Immunol. 2004; 113:115-9.

What is claimed is:

1. A method of treating or alleviating esophageal inflammation or symptoms of esophageal inflammation in an individual comprising orally administering to said individual a stable oral pharmaceutical composition comprising a topically active corticosteroid, a liquid vehicle and a mucoadhesive agent that increases the interaction of the composition with an esophageal surface, wherein the composition is chemically and physically stable, wherein the composition remains substantially uniform for at least 1 day; and wherein the individual has been diagnosed with Barrett's Esophagus, gastroesophageal reflux disease (GERD), nonerosive reflux disease (NERD), or erosive esophagitis.

* * * * *